United States Patent
Franco Rodriguez et al.

(10) Patent No.: US 12,226,485 B2
(45) Date of Patent: Feb. 18, 2025

(54) INJECTABLE COMPOSITION

(71) Applicant: Laboratorios Farmacéuticos ROVI, S.A., Madrid (ES)

(72) Inventors: Guillermo Franco Rodriguez, Madrid (ES); Ibon Gutierro Aduriz, Granada (ES)

(73) Assignee: Laboratorios Farmacéuticos ROVI, S.A., Madrid (ES)

( * ) Notice: Subject to any disclaimer, the term of this patent is extended or adjusted under 35 U.S.C. 154(b) by 1039 days.

(21) Appl. No.: 17/101,585

(22) Filed: Nov. 23, 2020

(65) Prior Publication Data

US 2021/0154302 A1 May 27, 2021

Related U.S. Application Data

(63) Continuation-in-part of application No. PCT/EP2019/065318, filed on Jun. 12, 2019.

(30) Foreign Application Priority Data

Jun. 12, 2018 (EP) ..................... 18382413

(51) Int. Cl.
*A61K 47/34* (2017.01)
*A61K 9/00* (2006.01)
(Continued)

(52) U.S. Cl.
CPC ............ *A61K 47/34* (2013.01); *A61K 9/0019* (2013.01); *A61K 31/426* (2013.01); *A61L 2/0017* (2013.01); *A61L 2/0029* (2013.01)

(58) Field of Classification Search
CPC .... A61K 47/34; A61K 9/0019; A61K 31/426; A61K 31/4196; A61K 9/0024; A61L 2/0017; A61L 2/0029
See application file for complete search history.

(56) References Cited

U.S. PATENT DOCUMENTS 3,636,956 A 1/1972 Schneider
3,773,919 A 11/1973 Boswell
(Continued)

FOREIGN PATENT DOCUMENTS

EP 2394663 A1 12/2011
WO WO 99/036071 A1 7/1999
(Continued)

OTHER PUBLICATIONS

Wang et al. ("Design of a long-term antipsychotic in situ forming implant and its release control method and mechanism", Int. J. Pharm., May 10, 2012;427(2):284-92).
(Continued)

*Primary Examiner* — Kyung S Chang
(74) *Attorney, Agent, or Firm* — INNOVAR, L.L.C.; Rick Matos

(57) ABSTRACT

An injectable depot composition suitable for forming an in situ intramuscular implant is provided. The composition includes sterile biodegradable thermoplastic polymer of polylactic acid (PLA), solvent for the PLA, and drug. After administration to a subject, a corresponding implant administers 0.1-2 milligrams of nonsteroidal aromatase inhibitor every day throughout a dosing period of about six months to about one year. The composition is used to treat subjects in need thereof.

15 Claims, 11 Drawing Sheets

(51) Int. Cl.
  *A61K 31/426*   (2006.01)
  *A61K 31/496*   (2006.01)
  *A61L 2/00*     (2006.01)

(56) References Cited

U.S. PATENT DOCUMENTS

| | | |
|---|---|---|
| 4,389,330 A | 6/1983 | Tice |
| 4,523,591 A | 6/1985 | Kaplan |
| 4,530,840 A | 7/1985 | Tice |
| 4,938,763 A | 7/1990 | Dunn |
| 5,620,700 A | 4/1997 | Bergren |
| 5,688,801 A | 11/1997 | Mesens |
| 5,770,231 A | 6/1998 | Mesens |
| 6,143,314 A | 11/2000 | Chandrashekar |
| 6,331,311 B1 | 12/2001 | Brodbeck |
| 6,528,080 B2 | 3/2003 | Dunn |
| 6,565,874 B1 | 5/2003 | Dunn |
| 6,630,155 B1 | 10/2003 | Chandrashekar |
| 6,673,767 B1 | 1/2004 | Brodbeck |
| 6,773,714 B2 | 8/2004 | Dunn |
| 6,803,055 B2 | 10/2004 | Mesens |
| 7,118,763 B2 | 10/2006 | Mesens |
| 8,076,448 B2 | 12/2011 | Moore |
| 8,221,778 B2 | 7/2012 | Siegel |
| 8,324,343 B2 | 12/2012 | Moore |
| 10,058,504 B2 | 8/2018 | Gutierro Aduriz et al. |
| 10,085,936 B2 | 10/2018 | Gutierro Aduriz et al. |
| 10,182,982 B2 | 1/2019 | Gutierro Aduriz et al. |
| 10,195,138 B2 | 2/2019 | Gutierro Aduriz et al. |
| 10,285,936 B2 | 5/2019 | Franco Rodriguez et al. |
| 10,335,366 B2 | 7/2019 | Gutierro Aduriz et al. |
| 10,350,159 B2 | 7/2019 | Gutierro Aduriz et al. |
| 10,463,607 B2 | 11/2019 | Gutierro Aduriz et al. |
| 10,881,605 B2 | 1/2021 | Gutierro Aduriz et al. |
| 10,912,735 B2 | 2/2021 | Franco Rodriguez et al. |
| 10,933,015 B2 | 3/2021 | Franco Rodriguez et al. |
| 2002/0009492 A1 | 1/2002 | Truong |
| 2002/0023409 A1 | 2/2002 | Py |
| 2003/0165571 A1 | 9/2003 | Alkermes |
| 2004/0010224 A1 | 1/2004 | Bodmeier |
| 2004/0247870 A1 | 12/2004 | Brown |
| 2005/0042294 A1 | 2/2005 | Thanoo |
| 2006/0121085 A1 | 6/2006 | Warren |
| 2006/0210604 A1 | 9/2006 | Dadey |
| 2007/0003596 A1 | 1/2007 | Tittelbach |
| 2007/0077304 A1 | 4/2007 | Luk |
| 2007/0275068 A1 | 11/2007 | Martens |
| 2008/0206303 A1 | 8/2008 | Gellert |
| 2008/0287464 A1 | 11/2008 | Wright |
| 2009/0264491 A1 | 10/2009 | McKay |
| 2009/0305957 A1 | 12/2009 | Moore |
| 2010/0015195 A1 | 1/2010 | Jain |
| 2010/0021544 A1 | 1/2010 | Bourges |
| 2010/0266655 A1 | 10/2010 | Dadey |
| 2010/0292195 A1 | 11/2010 | Dadey |
| 2012/0108511 A1 | 5/2012 | Moore |
| 2015/0147398 A1 | 5/2015 | Gutierro Aduriz et al. |
| 2015/0150791 A1 | 6/2015 | Gutierro Aduriz et al. |
| 2015/0196485 A1* | 7/2015 | Franco Rodriguez .......... A61K 9/0024 514/383 |
| 2019/0254960 A1 | 8/2019 | Gutierro Aduriz et al. |
| 2019/0321286 A1 | 10/2019 | Gutierro Aduriz et al. |
| 2019/0328654 A1 | 10/2019 | Gutierro Aduriz et al. |
| 2020/0085728 A1 | 3/2020 | Gutierro Aduriz et al. |
| 2021/0077380 A1 | 3/2021 | Gutierro Aduriz et al. |

FOREIGN PATENT DOCUMENTS

| | | |
|---|---|---|
| WO | WO 02/038185 A2 | 5/2002 |
| WO | WO 2007/041410 | 4/2007 |
| WO | WO 2008/059058 | 5/2008 |
| WO | WO 2008/153611 | 12/2008 |
| WO | 2009060473 A2 | 5/2009 |
| WO | 2009060473 A3 | 5/2009 |
| WO | WO 2011/151355 A1 | 12/2011 |
| WO | WO 2011/151356 A1 | 12/2011 |
| WO | WO 2013/178811 A1 | 12/2013 |
| WO | WO 2013/178812 A1 | 12/2013 |
| WO | 2014019972 A1 | 2/2014 |

OTHER PUBLICATIONS

Resomer products sheet of Evonik (2014) (http://www.resomer.com/product/biodegradable-polymers/en/pharma-polymers/products/pages/bioresorbable-polymer.aspx#Controlled release).

Maryott et al. (Table of Dielectric Constants of Pure Liquids, National Bureau of Standards, Circular No. 514, Aug. 10, 1951).

Gouw et al. (Physical Properties of Triglycerides IV. Dielectric Constant, Fette Seifen Anstrichmittel, (1967), 69(4), 223-226).

Lide (Properties of Common Laboratory Solvents, CRC Handbook of Chemistry and Physics 84th Ed., 2003-2004, Sect. 15-14, CRC Press, New York).

Resomer RG503 product literature (2014) (http://www.resomer.com/product/biodegradable-polymers/Specifications/evonik-specification-resomer-rg-503.pdf).

Resomer RG504 product literature (2014) (http://www.resomer.com/product/biodegradable-polymers/Specifications/evonik-specification-resomer-rg-504.pdf).

Resomer RG752S product literature (2014) (http://www.resomer.com/product/biodegradable-polymers/Specifications/evonik-specification-resomer-rg-752-s.pdf).

Resomer RG753S product literature (2014) (http://www.resomer.com/product/biodegradable-polymers/Specifications/evonik-specification-resomer-rg-753-s.pdf).

Jain et al. ("Injectable formulations of poly(lactic acid) and its copolymers in clinical use" in Adv. Drug. Deliv. Rev. (2016), 107, 213-227.

Kranz et al. ("A novel in situ forming drug delivery system for controlled parenteral drug delivery" in Inter. J. Pharm. (2007), 332(1-2), 107-114).

D'Souza et al. ("Methods to assess in vitro drug release from injectable polymeric particulate systems" in Pharm. Res. (2006), 23(3), 460-474).

Li et al. ("Microfluidic fabrication of microparticles for biomedical applications" in Chem. Soc. Rev. (2018), 47(15), 5646-5683).

Bassyouni et al. ("Advances and new technologies applied in controlled drug delivery system" in Res. Chem. Intermed. Inter. J. (2013), 41(4), 2165-2200).

Kissel et al. ("Parenteral depot-systems on the basis of biodegradable polyesters" in J. Control. Rel. (1991), 16(1-2), 27-41).

Gomathi et al. ("Fabrication of letrozole formulation using chitosan nanoparticles through ionic gelation method" in Inter. J. Biol. Macro. (2017), 104, 1820-1832).

Muralidhar ("Controlled release injectable drug delivery: an overview" in Asian J. Biomat. Res. (2017), 6-15).

\* cited by examiner

INJECTABLE COMPOSITION

CROSS-REFERENCE TO EARLIER FILED APPLICATIONS

The present application claims the benefit of and is a continuation-in-part of international application PCT/EP2019/065318 filed Jun. 12, 2019, which claims the benefit of European application EP 18382413.5 filed Jun. 12, 2018, the entire disclosures of which are hereby incorporated by reference.

FIELD OF THE INVENTION

The present patent application is directed toward compositions useful in cancer therapies. In particular, the present invention refers to the use of a letrozole composition suitable for forming an in situ intramuscular implant comprising a sterile biodegradable thermoplastic polymer of polylactic acid (PLA), for administering a patient in need thereof from 0.1-2 milligrams every day.

BACKGROUND OF THE INVENTION

Without doubt, cancer treatments need to be developed, not only new molecular entities but also pharmacological products for improving patients' quality of life. In this sense, the development of prolonged release formulation signifies an advance because they enable reducing the total dose administered, increasing the duration of each dose and the number of administrations and thereby create a positive impact on the emotional state of the patient.

In this sense, in the present invention, the active ingredients letrozole and anastrozole have been selected as candidate pharmaceutical drugs for this type of prolonged release formulation because they are the first line active ingredients in the adjuvant treatment of postmenopausal women with hormone receptor-positive advanced breast cancer for whom there is no alternative therapy beyond daily administration of a tablet.

Letrozole (4,4'-(1h,2,4-triazol-1-yl)methyl)dibenzonitrile) and anastrozole (2,2'-[5-(1H-1,2,4-triazol-1-yl methyl)-1,3-phenylene]bis(2-methylpropanenitrile)) belong to a class of drugs called non-steroidal inhibitors of aromatase and their mechanism of action consists of reducing the amount of estrogen in the body. This effect can decelerate or stop the growth of many types of cancer-producing cells in the breast that need estrogen to grow.

Currently there is no formulation of letrozole on the market with the ability to control the release of the drug over a long period of time. The pharmaceutical drug letrozole is currently only available in tablet form for daily oral administration (FEMARA®).

In the treatment of breast cancer, as in the treatment of cancer in general, the psychological state of the patient is very important; therefore the development of a three-monthly formulation of letrozole and/or anastrozole would result in a substantial improvement in their quality of life, reducing the impact that would result from daily treatment. In turn, medical examinations that are carried out during monitoring of the disease are normally conducted at 3 and 6 months over the first few years, so the administration of the formulation could coincide with consultancy visits to the doctor.

Similar reasoning has led to the appearance on the market of formulations such as ZOLADEX®, a preformed implant of goserelin for subcutaneous three-monthly application for the treatment of prostate carcinoma, and IMPLANON®, a preformed implant of etonogestrel used as a contraceptive. However, these preformed implants show a series of disadvantages including:

The preparation of the implants by extrusion requires the use of high temperatures, which can cause the degradation of the active ingredient and the generation of potentially toxic impurities;

Low homogeneity of the product obtained when including active ingredients at low doses;

Need for surgical procedures for implanting or injection of the implant using large diameter needles.

It is also possible to find in the literature some publications on implantable compositions of letrozole and/or anastrozole such as the following:

For example, WO 2008/041245 A2 published Apr. 10, 2008 to Panacea Biotec LTD describes implantable compositions comprising a wide variety of active ingredients such as some aromatase inhibitors, including anastrozole, in a wide variety of administration forms from preformed microparticles suspended in an aqueous vehicle to formulations that gellify in situ. Although it is doubtful that this document can sufficiently support all the combinations of active ingredients and administration forms that may arise, the examples always refer to preformed microparticles, that is it never describes systems of forming implants directly "in situ". Finally, it should be pointed out that none of the examples show a duration of over 60 days.

WO 2010/065358 A1 published Jun. 10, 2010 to Glaser describes compositions for the administration of medicines containing testosterone and an aromatase inhibitor for continuous administration of testosterone and for preventing its conversion to estradiol. Although the description considers the possibility that the form of administration may be an implant, the only example of a form of administration is pellets.

Also, WO 2012/074883 A1 published Jun. 7, 2012 to Durect Corp. describes biodegradable compositions for administration of pharmaceutical drugs. These compositions require the use of water-insoluble solvents such as benzyl benzoate or benzyl alcohol in order to maintain the implant in a liquid or semi-solid state. These solvents have been previously shown to provide sudden releases and therefore are not suitable for the prolonged release compositions of the present invention.

US 2008/0206303 A1 to Astra Zeneca describes prolonged release formulations of anastrozole comprising a PLA or PLGA polymer that can be accompanied by a wide variety of solvents; however, in the embodiments of the invention, the solvents used are benzyl alcohol and N-methyl-2-pyrrolidone (NMP), solvents that give rise to a very large burst followed by a subsequent almost zero release. In fact, the burst that was acceptable for the inventors in this document was 25-30% in one day, a very high value, and because of this none of their examples lasted more than 60 days; in particular in dogs, animals similar to humans, release did not continue longer than 35 days. Finally, no mention was made in this document of letrozole particle size nor of the importance of this factor in the behavior of the formulation.

Injectable compositions are disclosed by Jain et al. ("Injectable formulations of poly(lactic acid) and its copolymers in clinical use" in Adv. Drug Deliv. Rev. (2016), 107(14), 213-227), Kranz et al. ("A novel in situ forming drug delivery system for controlled parenteral drug delivery" in Inter. J. Pharma. (2007), 332(1-2), 107-114, D'Souza et al. ("Methods to assess in vitro drug release from injectable polymeric particulate systems" in Pharm. Res. (2006), 23(3), 460-474), Li et al. ("Microfluidic fabrication of microparticles for biomedical applications" in Chem. Soc. Rev. (2018), 47(15), 5646-5683), Bassyouni et al. ("Advances and new technologies applied in controlled drug delivery system" in Res. Chem. Interm. (2013), 41(4), 2165-2200), Kissel et al. ("Parenteral depot-systems on the basis of biodegradable polymers" in J. Contr. Rel. (1991), 16(1-2), 27-41), Gomathi et al. ("Fabrication of letrozole formulation using chitosan nanoparticles through ionic gelation method" in Inter. J. Biol. Macromol. (2017), 104(7), 1820-1832), and Muralidhar et al. ("Controlled release injectable drug delivery: an overview" in J. Biomat. Res. (2017), 3(1), 6-15).

Injectable compositions are also disclosed in WO 2014/019972A1, ES 2390439A1, U.S. Ser. No. 10/285,936B2, US 2019/0231682A1, US 2019/0365643A1, WO 2011/151356A2, EP 2394663A1, U.S. Ser. No. 10/058,504B2, US 2019/0151230A1, and U.S. Ser. No. 10/195,138B2, to Laboratorios Farmaceuticos ROVI, S.A. and WO2009060473A2 to Panacea Biotec Limited.

The particle size of the PLA polymer or PLGA copolymer has not been recognized as being associated with performance (burst release and length of period of extended release) of an implant formed from the injectable composition. Indeed, the polymer in the prior art injectable compositions is dissolved in solvent prior to administration, so one would not expect that the particle size of the polymer would have any impact upon performance of the corresponding implant(s).

Therefore, it would be desirable to obtain a three-monthly (trimesterly) formulation of letrozole and/or anastrozole for first line or adjuvant treatment of breast cancer in hormone receptor-positive postmenopausal women.

SUMMARY OF THE INVENTION

The present invention seeks to overcome the disadvantages of and/or to provide improvements over other injectable depot compositions comprising letrozole and/or anastrozole. The present invention includes injectable depot composition(s), implant(s) formed from said injectable depot composition(s), method(s) of forming said implant(s), kit(s) comprising components used to form said injectable depot composition(s), method(s) of administering letrozole and/or anastrozole by administering said injectable depot composition(s), and method(s) of treating disease(s), condition(s), or disorder(s) that is(are) therapeutically responsive to letrozole, anastrozole or metabolite of either thereof by administering said injectable depot composition(s).

The present invention relates to a letrozole-containing or anastrozole-containing composition suitable for forming one or more in situ intramuscular implants which can continuously maintain the required plasma levels of drug for hormone suppression during or for at least about 3 months or at least about 6 months. The implant formed in situ with the injectable composition of the invention overcomes the majority of the drawbacks presented by current formulations based on preformed implants. It offers an alternative practical and effective therapy for the patient achieving therapeutic profiles lasting for at least 60 days.

This long-term hormone suppression therapy has been shown to provide a superior clinical outcome in humans compared to oral daily dosage treatment. The formulations described herein enable obtaining therapeutic levels of the drug in plasma from the start and continuously over a period of at least six months, avoiding the need for daily oral dosing regimes and thereby improving the patient's quality of life.

Also, the invention provides a composition, and uses thereof, that provide a sustained lower, yet still effective drug, plasma levels with lower doses (compared to oral treatment on the basis of mg of drug per Kg of bodyweight) of the injectable composition. The reduced plasma levels reduce drug dose-related adverse side effects (bone mass loss, bone/joint/muscle pain, dyslipidemia) because of the lower exposure to drug due to the lower does, while still maintaining therapeutically effective plasma levels. Moreover, the present invention provides a better safety profile (lower incidence, lower frequency of occurrence, and/or lower severity of adverse events) which positively impacts treatment duration adherence.

The present inventors have found that the dose necessary for clinical efficacy of drug is much smaller than was thought or disclosed in the art. Thus, the compositions, and uses thereof, of the present invention provide an effective therapy for aromatase inhibition at least as early as the oral therapy from the time of administration, with much smaller doses than previous compositions, thereby providing a sustained and stable release of such low doses over long time periods (at least 6 months or at least 12 months) and reducing the adverse side effects.

An aspect of the invention provides a method of reducing adverse events associated with administration of certain dose of drug (letrozole, anastrozole, salt of either thereof, or metabolite of either thereof) in an extended release composition, the method comprising administering a lower dose of the drug in an injectable depot composition (or respective implant(s)) of the invention, whereby said lower dose provides lower adverse events but substantially the same efficacy as a higher dose of the drug in another injectable depot composition that is not of the invention.

After administration of the injectable composition and formation of the respective implant(s), said implant(s) can provide(s) a pharmacokinetic performance approximately (about) as follows:

| Dose of drug administered (mg) | About 50 | About 100 |
|---|---|---|
| Daily Plasma Concentration from about 2 days after administration (ng/mL) | About 4.5 (about 0.5 to about 13) | About 8.8 (about 1.5 to about 21) |
| Cmax (ng/mL) | About 5 | About 11 |
| Tlag (h) | 0 h | 0 h | wherein Tlag corresponds to the delay between the time of dosing and time of appearance of a measurable concentration of letrozole in the plasma. The above values are approximate and should be considered mean values.

The inventors of the present invention have found that the preferred clinically suitable and superior compositions are achieved when a particular particle size for the polymer is used. Said particle size was at first believed to be irrelevant to performance of the implant formed from the injectable composition, because the polymer is dissolved in the solvent when the injectable composition is prepared before administration. However, the inventors have found that the particle size of the polymer, in fact, has an impact upon the release of the active ingredient from the implant, and also has an impact upon the clinical suitability for the implant administration, since these type of compositions need to be administered by intramuscular injection soon after reconstitution. As shown in the figures, the present compositions with controlled particle size of the poly(lactic acid) (PLA) provide a drug release from the implant that allows having lower drug plasma levels which are still effective in hormone suppression and therefore can be used for longer periods and also reduce the adverse side effects.

The invention provides an injectable depot composition (and respective implant(s) thereof) and uses thereof that comprises a lower dose of drug, with respect to other injectable depot compositions not of the invention, while still providing therapeutically effective plasma levels of said drug for a period of at least six months.

The present invention relates to an injectable depot composition comprising PLA having a particle size distribution as follows: particle size mass distribution with not more than 10% above 300 microns, preferably not above 250 microns, when measured by analytical sieving according to USP<786> and/or said PLA has a particle size volume distribution with a D90 not above 330 microns, preferably not above 280 microns when measured by laser diffraction analysis; and/or wherein said PLA has a particle size mass distribution where not more than 80% of the particles have a particle size below 125 microns, when measured by analytical sieving according to USP<786> and/or said PLA has a particle size volume distribution with a D80 not below 135 microns when measured by laser diffraction analysis.

The present invention relates to a letrozole composition comprising a sterile biodegradable thermoplastic polymer of polylactic acid (PLA), wherein said PLA has optionally been sized and has a particle size mass distribution with not more than 10% above 300 microns, preferably not above 250 microns, when measured by analytical sieving according to USP<786>.

Also, the present invention relates to a letrozole composition comprising a sterile biodegradable thermoplastic polymer of polylactic acid (PLA), wherein said PLA has optionally been sized and has a particle size volume distribution with a D90 not above 330 microns, preferably not above 280 microns when measured by laser diffraction analysis.

Also, the present invention relates to a letrozole composition comprising a sterile biodegradable thermoplastic polymer of polylactic acid (PLA), wherein said PLA has optionally been sized and has a particle size mass distribution with not more than 10% above 300 microns, preferably not above 250 microns, and where not more than 80% of the particles have a particle size below 125 microns, when measured by analytical sieving according to USP<786>.

Also, the present invention relates to a letrozole composition comprising a sterile biodegradable thermoplastic polymer of polylactic acid (PLA), wherein said PLA has optionally been sized and has a particle size mass distribution where not more than 80% of the particles have a particle size below 125 microns, when measured by analytical sieving according to USP<786>.

Also, the present invention relates to a letrozole composition comprising a sterile biodegradable thermoplastic polymer of polylactic acid (PLA), wherein said PLA has optionally been sized and has a particle size volume distribution with a D90 not above 330 microns, preferably not above 280 microns when measured by laser diffraction analysis and with a D80 not below 135 microns when measured by laser diffraction analysis.

Also, the present invention relates to a letrozole composition comprising a sterile biodegradable thermoplastic polymer of polylactic acid (PLA), wherein said PLA has optionally been sized and has a particle size and/or said PLA has a particle size volume distribution with a D80 not below 135 microns when measured by laser diffraction analysis.

In a first aspect, the present invention relates to a stable sustained release letrozole composition for intramuscular administration suitable for forming an in situ intramuscular implant comprising from 10 to 500 mg of letrozole and a sterile biodegradable thermoplastic polymer of polylactic acid (PLA), wherein said PLA has been optionally sized; and/or wherein said PLA has a particle size mass distribution with not more than 10% above 300 microns, preferably not above 250 microns, when measured by analytical sieving according to USP<786> and/or said PLA has a particle size volume distribution with a D90 not above 330 microns, preferably not above 280 microns when measured by laser diffraction analysis; and/or wherein said PLA has a particle size mass distribution where not more than 80% of the particles have a particle size below 125 microns, when measured by analytical sieving according to USP<786> and/or said PLA has a particle size volume distribution with a D80 not below 135 microns when measured by laser diffraction analysis; and wherein the percentage of active agent released from the implant is ranges from about 2-30% each 28-day interval for at least three to four intervals, preferably from about 5-25% each 28-day interval for at least three to four intervals; and/or wherein the composition releases from 0.1 to 2 milligrams of letrozole every day, preferably from 0.13 to 0.80 milligrams of letrozole every day.

In some embodiments, an implant comprising about 50 mg of letrozole releases an average of about 0.1-0.15, about 0.12-0.14, or about 0.13 mg of letrozole per day for a period of at least about 337-365 days, wherein the average is based upon daily release of drug throughout entire said period. In some embodiments, an implant comprising about 100 mg of letrozole releases an average of about 0.2-0.3, about 0.24-0.28, or about 0.27 mg of letrozole per day for a period of at least about 337-365 days, wherein the average is based upon daily release of drug throughout entire said period.

In some embodiments, the implant releases an average of about 10-15% of its charge per 28-day interval for the first four intervals and then an average of about 2-6% of its charge per 28-day interval for the following eight to nine intervals. In some embodiments, the implant releases no more than about 60% (or no more than about 55%, or no more than about 50%) of its charge of letrozole within the first 112 days (four 28-day intervals) and releases the remainder of its charge of letrozole at a rate of about 2-6% per 28-day interval for 8 to 9 intervals (about 224 days to about 252 days). In some embodiments, the implant releases its charge of letrozole over a period of at least about one year, at least about 365 days, or at least about twelve to thirteen 28-day intervals. In some embodiments, the implant releases about 40-55% or about 40-50% of its charge of letrozole during the first 3-4 months and about 60-45% or about 60-50%, respectively, of its charge during the following 8-9 months. In some embodiments, the implant releases up to a total of about 30% of its charge during the first 28-day interval, up to a total of about 40% of its charge during the second 28-day interval, up to a total of about 50% of its charge during the third 28-day interval, up to a total of about 55% during the fourth 28-day interval, then an average of about 2-6% of its charge per 28-day interval for the following eight to nine intervals. In some embodiments, the implant releases up to a total of about 20-35% of its charge during the first 28-day interval, up to a total of about 25-40% of its charge during the second 28-day interval, up to a total of 35-50% of its charge during the third 28-day interval, up to a total of about 40-55% during the fourth 28-day interval, then an average of about 2-6% of its charge per 28-day interval for the following eight to nine intervals.

In some embodiments, the implant releases letrozole according to any of the following profiles.

| 28-day interval | Percentage of letrozole released* | Percentage of letrozole released* | Mean or average of percentage of letrozole released* |
|---|---|---|---|
| 1st | 7-15 | 9-13 | About 11-12 |
| 2nd | 5-12 | 6-11 | About 7.5-8.5 |
| 3rd | 2-9 | 3-8 | About 3.5-7.5 |
| 4th and on for each interval through final interval for at least 8 intervals | 0.5-6 | 1-6 | About 2-6 |
| 1st | Up to 25 | Up to 15 | Up to 13 |
| 2nd | Up to 18 | Up to 13 | Up to 11 |
| 3rd | Up to 12 | Up to 10 | Up to 8 |
| 4th and on for each interval through final interval for at least 8 intervals | Up to 10 | Up to 8 | Up to 6 |

*wherein the percentage is relative to the initial charge of letrozole in the implant.

In a preferred embodiment, the injectable composition comprises a water miscible solvent, wherein the solvent is preferably dimethyl sulfoxide (DMSO).

In a preferred embodiment, the stable sustained release letrozole composition of the first aspect is characterized in that said composition releases up to 30% of the letrozole in 30 days, preferably up to 25% of the letrozole in 30 days; or up to 50% of the letrozole in 100 days, preferably in 120 days and more preferably in 130 days; or said composition releases up to 80% of the letrozole in 140 days, preferably in 180 days, more preferably in 200 days; or composition releases up to 80% of the letrozole in 240 days, in an in vitro dissolution test performed with horizontal orbital motion at 50 rpm; medium: PBS pH 7.4; temperature: 37±0.5° C.; analytical technique: HPLC/UV; wavelength 230 nm.

In a preferred embodiment, the composition comprises from 10 to 450 mg of letrozole. In a preferred embodiment, the composition comprises from 30 to 90 mg or about 50 mg of letrozole. In a preferred embodiment, the composition comprises from 80 to 150 mg or about 100 mg of letrozole. In a preferred embodiment, the composition comprises from 150 to 250 mg or about 200 mg of letrozole. In a preferred embodiment, the composition comprises from 350 to 450 mg or about 400 mg of letrozole.

In a preferred embodiment, the end group of the PLA is an ester group.

In a preferred embodiment, the particle size distribution of letrozole is such that less than 10% of the particles have a size below 20 microns, less than 10% of the particles have a size greater than 350 microns and the D50 is between 70-200 microns, when measured by laser diffraction analysis (volume distribution).

An aspect of the invention also provides a kit comprising drug, PLA, and solvent for PLA, wherein the particle size distribution for said drug approximates the particle size distribution for said PLA. Said particle size distributions may be a combination of any of the particle size distributions disclosed herein.

In a preferred embodiment, the composition comprises 5-40 wt. % letrozole, 20-40 wt. % PLA, 20-80 wt. % DMSO, with respect to the total weight of the composition before administration. Preferably, the composition comprises 15-35 wt. % letrozole, 25-35 wt. % PLA and 30-60 wt. % DMSO, with respect to the total weight of the composition before administration. Preferably, the composition comprises 18-28 wt. % letrozole, 30-35 wt. % PLA and 37-52 wt. % DMSO, with respect to the total weight of the composition before administration. Alternatively, the composition comprises about 23 to about 27 wt. % letrozole, about 28 to about 34 wt. % PLA, and about 41 to about 47 wt. % DMSO, with respect to the total weight of the composition before administration. The composition may also comprise about 24 to about 26 wt. % letrozole, about 29 to about 33 wt. % PLA, and about 42 to about 47 wt. % DMSO, with respect to the total weight of the composition before administration.

A preferred embodiment of the first aspect of the invention relates to a stable sustained release letrozole composition for intramuscular administration suitable for forming an in situ intramuscular implant comprising, preferably consisting essentially of, preferably consisting of: from 30 to 90 mg of letrozole, DMSO and a sterile biodegradable PLA, wherein the end group of the PLA is an ester group, wherein said PLA has a particle size mass distribution with not more than 10% above 300 microns, preferably not above 250 microns, when measured by analytical sieving according to USP<786> and wherein said PLA has a particle size mass distribution where not more than 80% of the particles have a particle size below 125 microns, when measured by analytical sieving according to USP<786> and wherein the release of the active agent from the implant is between 2 and 30% of the active agent each 28-day interval, preferably is between 5 and 25% of the active agent each 28-day interval; and wherein the particle size of letrozole is such that less than 10% of the particles have a size below 20 microns, less than 10% of the particles have a size greater than 350 microns and the D50 is between 70-200 microns, when measured by laser diffraction analysis (volume distribution); and wherein the composition comprises 15-35 wt. % letrozole, 25-35 wt. % PLA and 30-60 wt. % DMSO, with respect to the total weight of the composition before administration; and wherein the composition releases from 0.1 to 2 milligrams of letrozole every day; and wherein the stable sustained release composition provides a plasma level of letrozole between about 1 to about 40 ng/ml from about 2 days after the implant administration and continuously throughout a dosing period. The release of letrozole from this embodiment may be as otherwise specified herein.

A preferred embodiment of the first aspect of the invention relates to a stable sustained release letrozole composition for intramuscular administration suitable for forming one or more in situ intramuscular implant(s) comprising, preferably consisting essentially of, preferably consisting of: from 80 to 150 mg of letrozole, DMSO and a sterile biodegradable PLA, wherein the end group of the PLA is an ester group, wherein said PLA has a particle size mass distribution with not more than 10% above 300 microns, preferably not above 250 microns, when measured by analytical sieving according to USP<786> and wherein said PLA has a particle size mass distribution where not more than 80% of the particles have a particle size below 125 microns, when measured by analytical sieving according to USP<786> and wherein the release of the active agent from the implant is between 2 and 30% of the active agent each 28-day interval, preferably is between 5 and 25% of the active agent each 28-day interval; and wherein the particle size of letrozole is such that less than 10% of the particles have a size below 20 microns, less than 10% of the particles have a size greater than 350 microns and the D50 is between 70-200 microns, when measured by laser diffraction analysis (volume distribution); and wherein the composition comprises 15-35 wt. % letrozole, 25-35 wt. % PLA and 30-60 wt. % DMSO, with respect to the total weight of the composition before administration; and wherein the composition releases from about 0.1 to about 2 milligrams of letrozole every day throughout a dosing period; and wherein the stable sustained release composition provides a plasma level of letrozole between about 1 to about 40 ng/ml from about 2 days after the implant administration and continuously throughout a dosing period. The release of letrozole from this embodiment may be as otherwise specified herein.

A preferred embodiment of the first aspect of the invention relates to a stable sustained release letrozole composition for intramuscular administration suitable for forming one or more in situ intramuscular implant(s) comprising, preferably consisting essentially of, preferably consisting of: from 150 to 250 mg of letrozole, DMSO and a sterile biodegradable PLA, wherein the end group of the PLA is an ester group, wherein said PLA has a particle size mass distribution with not more than 10% above 300 microns, preferably not above 250 microns, when measured by analytical sieving according to USP<786> and wherein said PLA has a particle size mass distribution where not more than 80% of the particles have a particle size below 125 microns, when measured by analytical sieving according to USP<786> and wherein the release of the active agent from the implant is between 2 and 30% of the active agent each 28-day interval, preferably is between 5 and 25% of the active agent each 28-day interval; and wherein the particle size of letrozole is such that less than 10% of the particles have a size below 20 microns, less than 10% of the particles have a size greater than 350 microns and the D50 is between 70-200 microns, when measured by laser diffraction analysis (volume distribution); and wherein the composition comprises 15-35 wt. % letrozole, 25-35 wt. % PLA and 30-60 wt. % DMSO, with respect to the total weight of the composition before administration; and wherein the composition releases from 0.1 to 2 milligrams of letrozole every day of a dosing period; and wherein the stable sustained release composition provides a plasma level of letrozole between about 1 to about 40 ng/ml from about 2 days after the implant administration and continuously throughout a dosing period. The release of letrozole from this embodiment may be as otherwise specified herein.

A preferred embodiment of the first aspect of the invention relates to a stable sustained release letrozole composition for intramuscular administration suitable for forming one or more in situ intramuscular implant comprising, preferably consisting essentially of, preferably consisting of: from 350 to 450 mg of letrozole, DMSO and a sterile biodegradable PLA, wherein the end group of the PLA is an ester group, wherein said PLA has a particle size mass distribution with not more than 10% above 300 microns, preferably not above 250 microns, when measured by analytical sieving according to USP<786> and wherein said PLA has a particle size mass distribution where not more than 80% of the particles have a particle size below 125 microns, when measured by analytical sieving according to USP<786> and wherein the release of the active agent from the implant is between 2 and 30% of the active agent each 28-day interval, preferably is between 5 and 25% of the active agent each 28-day interval; and wherein the particle size of letrozole is such that less than 10% of the particles have a size below 20 microns, less than 10% of the particles have a size greater than 350 microns and the D50 is between 70-200 microns, when measured by laser diffraction analysis (volume distribution); and wherein the composition comprises 15-35 wt. % letrozole, 25-35 wt. % PLA and 30-60 wt. % DMSO, with respect to the total weight of the composition before administration; and wherein the composition releases from 0.1 to 2 milligrams of letrozole every day of a dosing period; and wherein the stable sustained release composition provides a plasma level of letrozole between about 1 and about 40 ng/ml from about 2 days after the implant administration and continuously throughout a dosing period. The release of letrozole from this embodiment may be as otherwise specified herein.

In a preferred embodiment, the letrozole and the PLA are combined into a first component (first syringe) of the composition and the solvent is a separate second component (second syringe) of the composition. The injectable depot composition is then formed by mixing the two components.

In another aspect, the present invention relates to a kit suitable for the in situ preparation of the composition of the first aspect, comprising at least two containers or syringes, wherein the first container or syringe comprises the letrozole and the PLA, and the second container or syringe comprises the solvent, preferably DMSO. The injectable depot composition is then formed by mixing the contents of at least the first and second containers.

In a second aspect, the present invention relates to a process for preparing the stable sustained release letrozole composition of the first aspect, comprising mixing the components of the composition prior to administration. The components can be mixed as long as desired, or for 30 min or more, 30 min or less, 20 min or less, 15 in or less, preferably 10 minutes or less, and more preferably 5 minutes or less prior to administration. In a preferred embodiment, active ingredient and PLA are provided together and that combination is mixed with the solvent.

In a preferred embodiment, the composition after preparation is a suspension. Preferably, the drug is in suspension and the PLA is dissolved in the solvent.

In a preferred embodiment, the composition is prepared by mixing the solvent, preferably DMSO, with a previous solid combination (mixture) of letrozole and PLA. In a preferred embodiment of the third aspect, the composition is prepared (reconstituted) by first mixing the active agent with the PLA and then adding the solvent.

In a third aspect, the present invention relates to the use of the stable sustained release composition of the first aspect for administering to a subject from 0.1-2 milligrams of letrozole every day and continuously throughout a dosing period.

The invention also provides a method of administering letrozole to a subject. The method comprises providing a composition (as defined herein) comprising (consisting essentially of or consisting of) letrozole, DMSO, and PLA, and administering said composition to the subject. The method of administration can be separate from a method of treatment. The method of administration may also be part of a method of treatment. The release of letrozole from the implant (sustained release composition) may be as specified herein.

Following administration, the injectable composition will form one or more implants. The composition can be administered to adipose tissue, muscle tissue, below the skin, or in the peritoneum.

In a preferred embodiment, the stable sustained release composition of the first aspect is used for administering to a subject, optionally a subject in need thereof, from 0.1-1.25 milligrams (mg) of letrozole every day and continuously throughout a dosing period. Preferably, the stable sustained release composition of the first aspect is used for administering a subject, optionally a subject in need thereof, from 0.1 to 1.20 mg, preferably from 0.13 to 1.15 mg, more preferably from 0.13 to 1.10 mg, even more preferably from 0.13 to 0.8 mg of letrozole every day and continuously throughout a dosing period, following formation of one or more implants from said composition. The release of letrozole may be as otherwise specified herein.

In a preferred embodiment, the stable sustained release composition of the first aspect provides a plasma level of letrozole between about 1 and about 40 ng/ml from about 2 days after administration and continuously throughout a dosing period. Preferably, the stable sustained release composition of the first aspect forms one or more implants and provides a plasma level of letrozole between about 1 and about 40 ng/ml from about 2 days after administration and continuously throughout a dosing period of at least six months, or from 6 to 12 months, or of at least 12 months. In some embodiments, the implant or sustained release composition of the invention provides measurable and therapeutic plasma concentrations levels of letrozole for at least about 2 years, at least about 2.5 years, at least about 2.7 years or at least about 2.8 years.

In a preferred embodiment, the stable sustained release composition of the first aspect forms one or more implants and provides a plasma level of letrozole between about 1.5 and about 30 ng/ml from about 2 days after administration and continuously throughout a dosing period. Preferably, the stable sustained release composition of the first aspect forms one or more implants and provides a plasma level of letrozole between about 1.5 and about 30 ng/ml from about 2 days after administration and continuously throughout a dosing period of at least six months, or from 6 to 12 months, or of at least 12 months.

In a preferred embodiment, the stable sustained release composition of the first aspect forms one or more implants and provides a plasma level of letrozole between about 1.5 and about 25 ng/ml from about 2 days after administration and continuously throughout a dosing period. Preferably, the stable sustained release composition of the first aspect forms one or more implants and provides a plasma level of letrozole between about 1.5 and about 25 ng/ml from about 2 days after administration and continuously for at least six months, or from 6 to 12 months, or at least 12 months.

In a preferred embodiment, the stable sustained release composition of the first aspect forms one or more implants and provides a plasma level of letrozole between about 1.5 and about 20 ng/ml from about 2 days after administration and continuously throughout a dosing period. Preferably, the stable sustained release composition of the first aspect forms one or more implants and provides a plasma level of letrozole between about 1.5 and about 20 ng/ml from about 2 days after administration and continuously throughout a dosing period of at least six months, or from 6 to 12 months, or of at least 12 months.

In a preferred embodiment, the stable sustained release composition of the first aspect forms one or more implants and provides a plasma level of letrozole between about 1.5 and about 15 ng/ml from about 2 days after administration and continuously throughout a dosing period. Preferably, the stable sustained release composition of the first aspect forms one or more implants and provides a plasma level of letrozole between about 1.5 and about 15 ng/ml from about 2 days after administration and continuously throughout a dosing period of at least six months, or from 6 to 12 months, or of at least 12 months.

In a preferred embodiment, the stable sustained release composition of the first aspect provides forms one or more implants and a plasma level of letrozole between about 1.5 and about 10 ng/ml from about 2 days after administration and continuously throughout a dosing period. Preferably, the stable sustained release composition of the first aspect forms one or more implants and provides a plasma level of letrozole between about 1.5 and about 10 ng/ml from about 2 days after administration and continuously throughout a dosing period of at least six months, or from 6 to 12 months, or of at least 12 months.

In a preferred embodiment, the stable sustained release composition of the first aspect is used for suppressing estradiol plasma levels to less than 1 pg/ml after 4 days from the implant administration and continuously thereon throughout a dosing period. Said suppressed estradiol plasma level is maintained for at least 1 month, preferably at least 3 months, at least six months, from about 6 to about 12 months, at least 12 months, continuously from about 1 to about 12 months, continuously from about 9 to about 12 months, more preferably continuously from about 1 to about 10 months, even more preferably continuously from about 1 to about 6 months.

In a preferred embodiment, the stable sustained release composition of the first aspect forms one or more implants that release the drug with an immediate onset of action and continuously for at least 1 month, preferably at least 3 months, more preferably at least 6 months, even more preferably at least 12 months. In a preferred embodiment, the stable sustained release composition of the first aspect forms one or more implants that release the drug with an immediate onset of action and continuously from about 1 to about 12 months or from about 9 to about 12 months, more preferably from about 1 to about 10 months, even more preferably from about 1 to about 6 months.

In a preferred embodiment, the stable sustained release composition of the first aspect forms one or more implants and releases the drug with an immediate onset of action and continuously throughout a dosing period of about 3 to about 6 months.

In a preferred embodiment, the stable sustained release composition of the first aspect is formed from an injectable intramuscular depot and sterile composition suitable for forming one or more in situ solid, semisolid or gel implant(s) in a subject. In a preferred embodiment, the stable sustained release composition is a single implant.

The composition(s) and implant(s) of the invention are preferably used in humans.

In another aspect, the present invention relates to the use of a letrozole-containing composition suitable for forming an in situ intramuscular implant comprising a sterile biodegradable thermoplastic polymer of polylactic acid (PLA), for administering to a subject from about 0.1 to about 2 milligrams every day throughout a dosing period of. Preferably, the use is for administering to a subject from about 0.13 to about 1.25 milligrams every day throughout a dosing period of.

In a preferred embodiment, the composition forms one or more implants and provides a plasma level of letrozole about 1 to about 40 ng/ml after 2 days from administration and continuously throughout a dosing period. More preferably, the composition forms one or more implants and provides a plasma level of letrozole from about 1.5 to about 30 ng/ml after 2 days from administration and continuously throughout a dosing period.

In a preferred embodiment of this aspect, the composition (the one or more implants formed therefrom) is used for suppressing estradiol plasma levels to less than about 1 pg/ml after 4 days from the implant administration and continuously throughout a dosing period.

In a preferred embodiment of this aspect, the composition is used for aromatase inhibition, preferably in humans. In a preferred embodiment of this aspect, the composition is used for treating breast cancer. In a preferred embodiment of this aspect, the composition is used for adjuvant treatment of postmenopausal women with hormone receptor positive early breast cancer or for extended adjuvant treatment of postmenopausal women with early breast cancer who have received prior standard adjuvant tamoxifen therapy, or for first and second-line treatment of postmenopausal women with hormone receptor positive or unknown advanced breast cancer or any combination thereof.

The invention also provides a method of treating a disease, disorder or condition that is therapeutically responsive to nonsteroidal inhibitor of aromatase, which can be selected from the group consisting of letrozole, anastrozole, and a metabolite of either thereof. The disease, disorder or condition may be selected from the group consisting of hormonally-responsive breast cancer, local or metastatic breast cancer that is hormone receptor positive or has an unknown receptor status in postmenopausal women, hormone receptor positive early breast cancer in postmenopausal women, early breast cancer in postmenopausal women who have received prior standard adjuvant tamoxifen therapy, advanced breast cancer in postmenopausal women with disease progression following tamoxifen therapy, ER-negative disease in subjects who did not respond to previous tamoxifen therapy, gynecomastia, and endometriosis. The breast cancer can be early-stage breast cancer or advanced-stage (late-stage) breast cancer. The composition may be administered as part of adjuvant therapy, first-line therapy, or second-line therapy. The composition may also be used to induce ovulation in a female subject or to promote spermatogenesis in a male subject (e.g. one suffering from nonobstructive azoospermia).

In some embodiments, the subject in need thereof is a woman with breast cancer, optionally a postmenopausal woman with breast cancer. In some embodiments, the subject is not also being concurrently administered tamoxifen. The composition of the invention may be administered before and/or after surgery in a subject.

Another aspect of the present invention relates to a letrozole composition for intramuscular administration comprising a sterile biodegradable thermoplastic polymer of polylactic acid (PLA), wherein the composition releases from 0.1-2 milligrams every day and continuously throughout a dosing period.

In a preferred embodiment of this aspect, the composition releases the drug with an immediate onset of action and continuously for at least 1 month, preferably at least 3 months, more preferably at least 6 months, even more preferably at least 12 months. In a preferred embodiment of this aspect, the composition releases the drug with an immediate onset of action and continuously for at least 1 month, at least 2 months, at least 3 months, at least 4 months, at least 5 months, at least 6 months, at least 7 months, at least 8 months, at least 9 months, at least 10 months, at least 11 months or at least 12 months. In a preferred embodiment, the composition releases the drug with an immediate onset of action and continuously for at least 12 months. In another preferred embodiment, the composition releases the drug with an immediate onset of action and continuously between about 3 and about 6 months.

In a preferred embodiment of this aspect, the composition is a sterile injectable intramuscular depot composition suitable for forming an in situ solid, semisolid or a gel implant in a body.

The present invention relates to a letrozole composition suitable for forming an in situ intramuscular implant which can maintain the required letrozole plasma levels for hormone suppression during at least 6 months throughout a dosing period.

This long-term sustained hormone suppression therapy has been shown to provide a superior clinical outcome in humans compared to oral daily dosage treatment. Also, sustained lower effective letrozole plasma level with lower doses (compared to oral treatment) reduce the adverse side effects (bone mass loss, bone/joint/muscle pain, dyslipidemia) due to lower exposure to drug. Moreover, the present invention provides a better safety profile which positively impact treatment duration adherence.

Clauses

1.—Use of a letrozole composition suitable for forming an in situ intramuscular implant comprising a sterile biodegradable thermoplastic polymer of polylactic acid (PLA), for administering a patient in need thereof from 0.1-2 milligrams every day.

2.—The use according to the preceding clause, for administering a patient in need thereof from 0.1-1.25 milligrams every day.

3.—The use according to any one of the preceding clauses, wherein the composition forms one or more implants and provides a plasma level of letrozole between 1 and 40 ng/ml after 2 days from administration.

4.—The use according to any one of the preceding clauses, wherein the composition forms one or more implants and provides a plasma concentration of letrozole between 1.5 and 30 ng/ml after 2 days from administration.

5.—The use according to any one of the preceding clauses for suppressing estradiol plasma levels to less than 1 pg/ml after 4 days from administration.

6.—A letrozole composition for intramuscular administration comprising a sterile biodegradable thermoplastic polymer of polylactic acid (PLA), wherein the composition forms one or more implants after administration and releases from 0.1-2 milligrams every day.

7.—A letrozole composition for intramuscular administration comprising a sterile biodegradable thermoplastic polymer of polylactic acid (PLA) according to clause 6 wherein the composition forms one or more implants after administration and releases the drug with an immediate onset of action and continuously for at least 1 month, preferably at least 3 months, more preferably at least 6 months, even more preferably at least 12 months.

8.—A letrozole composition according to any one of the preceding clauses 6 or 7 wherein the composition forms one or more implants after administration and releases the drug with an immediate onset of action and continuously between 3 and 6 months.

9.—A letrozole composition according to any one of the preceding clauses 6 to 8 wherein the composition is an injectable intramuscular depot and sterile composition suitable for forming an in situ solid, semisolid or a gel implant in a body.

10.—A letrozole composition according to any one of the preceding clauses 6 to 9, wherein said PLA is milled; and/or wherein said PLA has a particle size mass distribution with not more than 10% above 300 microns, preferably not above 250 microns, when measured by analytical sieving according to USP<786> and/or with a D90 in volume not above 330 microns, preferably not above 280 microns when measured by laser diffraction analysis; and/or wherein said PLA has a particle size distribution where not more than 80% in mass of the particles have a particle size below 125 microns, when measured by analytical sieving according to USP<786> and/or with a D80 in volume not below 135 microns when measured by laser diffraction analysis.

11.—A letrozole composition according to any one of the preceding clauses 6 to 10, characterized in that said composition releases up to 30% of the letrozole in 30 days, preferably up to 25% of the letrozole in 30 days; or up to 50% of the letrozole in 100 days, preferably in 120 days and more preferably in 130 days; or said composition releases up to 80% of the letrozole in 140 days, preferably in 180 days, more preferably in 200 days; or composition releases up to 80% of the letrozole in 240 days, in an in vitro dissolution test performed with horizontal orbital motion at 50 rpm; medium: PBS pH 7.4.; temperature: 37±0.5° C.; analytical technique HPLC/UV; wavelength 230 nm.

The invention includes all combinations of the aspects, embodiments, sub-embodiments and clauses disclosed herein. Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

FIG. 2 depicts a chart of letrozole plasma levels (ng/ml) observed versus time after administration of FEMARA® or the composition of the invention (Letrozole ISM). The composition of the invention provided a substantially longer sustained letrozole plasma levels. Letrozole plasma levels (ng/ml) observed after administering Femara® or the.

Figure 1:
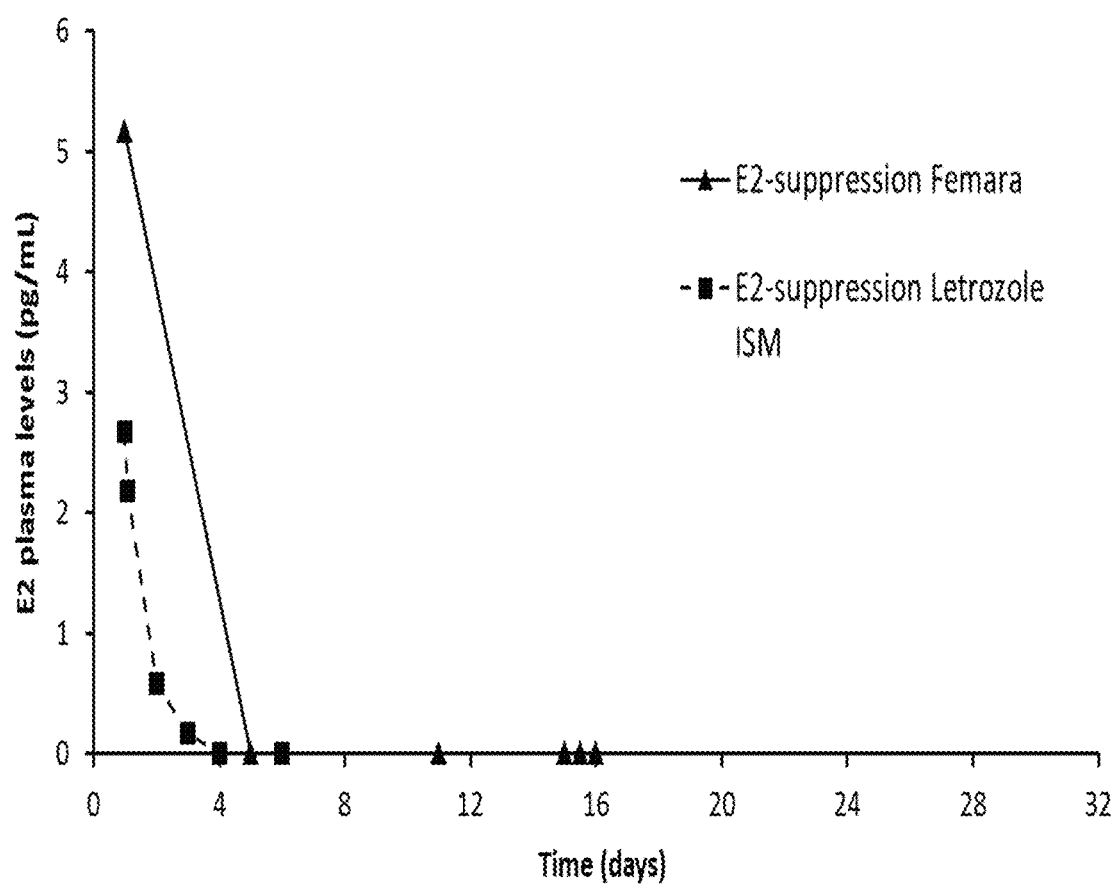
FIG. 1 depicts a chart of estradiol (E2) plasma levels (pg/ml) observed versus time after administration of FEMARA® or the composition of the invention (Letrozole ISM). More rapid and sustained estradiol suppression were achieved using substantially lower doses of the composition of the invention (and/or substantially lower plasma levels of letrozole) as compared to FEMARA® dose and plasma level of letrozole.

An overlay of the charts of FIGS. 6A, 6B, 7A, and 7B depict the plasma levels of E1 (estrone) and E2 (estradiol).

DETAILED DESCRIPTION OF THE INVENTION

As used herein, the terms "disease, disorder or condition that is therapeutically responsive to nonsteroidal inhibitor of aromatase" excludes any disease, disorder or condition that is not therapeutically responsive to nonsteroidal inhibitor of aromatase. The therapeutic responsive of said disease, disorder or condition to nonsteroidal inhibitor of aromatase is determined by administering one or more compositions of the invention to a subject in need thereof, wherein the dose of drug (via the composition) is administered as defined herein to provide one or more implants that release said nonsteroidal inhibitor of aromatase for the period of time as defined herein to provide the plasma levels of said drug or metabolite thereof as defined herein. A clinician then determines whether said disease, disorder or condition responds therapeutically, meaning the clinician determines whether the subject in need has experienced the desired clinical benefit(s). For example, when treating cancer, a therapeutic response may include slowing or reversing the progression of the cancer or might even include remission of the cancer. When treating gynecomastia, a therapeutic response may include reduction in breast size or slowing down the enlargement of the breast. A clinician familiar with nonsteroidal inhibitors of aromatase will be able to follow methods and conventions of the art to determine whether said disease, disorder or condition is therapeutically responsive to said nonsteroidal inhibitor of aromatase.

As used herein, the term "dosing period" refers to the period from administration of injectable depot composition to termination of release of drug from a corresponding one or more implants. As used herein, the term "treatment period" refers to the period during which a subject receives dose(s) of the injectable depot composition. A treatment period may comprise one or more dosing periods during which time the subject receives one or more corresponding doses.

As used herein, the terms "letrozole" and "anastrozole" refers to the non-salt and salt forms thereof. The term "active ingredient", "active agent", or "drug" refers to a therapeutically active compound, as well as any, derivatives thereof, prodrugs thereof, and pharmaceutically acceptable salts, hydrates and solvates of said compound, derivative(s), and prodrug(s). In the present invention, the active agent is letrozole and/or anastrozole.

The term "stable sustained release composition" generally refers to the one or more implant(s), which together provide a dose of drug during a dosing period.

The term "stable" as used herein refers to a pharmaceutical composition comprising letrozole wherein the total content of impurities originating from the decomposition of letrozole does not exceed 5% area, preferably 3% area, more preferably 2% area and most preferably 1% area determined by liquid chromatography (HPLC) at 230 nm if such a composition is stored for 2 months at 40° C. and 75% relative humidity (RH).

The inventors have unexpectedly determined that the particle size distribution of the PLA (polylactic acid) polymer used in the composition (and corresponding implant(s)) of the invention has an impact upon in vitro and in vivo performance of the implant(s).

As used herein, "sized" PLA (pr "PLA that has been sized) is PLA that has been processed to provide a particular particle size distribution as described herein. Sizing of the PLA is optional. Methods of sizing PLA, include by way of example and without limitation, milling, comminuting, sieving, classifying, grinding, impacting, homogenizing, sonicating, ultrasonicating, dry milling, wet milling, cryogenic milling or other such processes known in the art of particle size reduction.

When the PLA particle size is measured by analytical sieving according to USP<786>, the amplitude is 0.65 mm and the shaking time is 5 minutes. When the PLA particle size is measured by laser diffraction analysis, the particle size is determined by wet dispersion method. No sample pre-treatment was applied. The sample was directly added into the dispersion medium (water). Dispersion mechanism was stirring at 3000 rpm.

The PLA polymer is selected from free acid (not end-capped; uncapped) or end-capped (e.g. alkyl esters such as lauryl ester, methyl ester, etc., referred to herein as PLA-e) terminal carboxylic poly-lactide with polymer. The PLA polymer can be a poly(L-lactic acid) polymer, poly(D,L-lactic acid) polymer, poly (D-lactic acid) or a copolymer of those polymers. Polymers that are end-capped with esters (as opposed to the free carboxylic acid) demonstrate longer degradation half-lives; even so, uncapped polymers having carboxylic acid terminal groups also exhibit the particle size-related improved performance. Suitable grades of PLA are commercially available from Uhde Inventa-Fischer (Berlin, DE), NatureWorks LLC (Blair, NE, USA), Plastic Ingenuity (Cross Plains, WI, USA), Toyobo, Dai Nippon Printing Co., Mitsui Chemicals, Shimadzu, NEC, Toyota (Japan), PURAC Biomaterials, Hycail (The Netherlands), Galactic (Belgium), Cereplast (U.S.A.), FkuR, Biomer, Stanelco, Inventa-Fischer (Germany), Snamprogetti (China), Boehringer Ingelheim (RESOMER® grades; Ingelheim Am Rhein, DE), Evonik Industries (RESOMER® grades; Essen, DE), ALKERMES (Dublin, Ireland) or SIGMA ALDRICH (ST. Louis, MO). In some embodiments, the PLA is end-capped with an alkyl alcohol to form an ester end group moiety.

The PLA polymer exhibits an inherent or intrinsic viscosity in the range of about 0.16-0.60 dl/g, or about 0.20-0.50 dl/g as measured in chloroform at 25° C. at a concentration of 0.1% wt/v with a Ubbelhode size 0c glass capillary viscometer or as measured in chloroform at 30° C. and at a concentration of 0.5% wt/v with a size 25 Cannon-Fenske glass capillary viscometer. The inherent viscosity can be as measured before or after beta irradiation, if such irradiation is employed.

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. The injectable composition comprises (or consists essentially or consists of) solvent, PLA polymer and drug. Accordingly, the injectable composition comprises (or consists essentially or consists of) polymeric solution and drug.

In some embodiments, the polymeric solution has a minimum viscosity of about 0.8 Pa·s, although this may preferably be around 1 Pa·s. The viscosity can be about 4 Pa·s or less, about 3 Pa·s or less, about 2 Pa·s or less, about 1.8 Pa·s or less. The viscosity of the polymer solution can range from about 0.7 to about 4 Pa·s, about 0.7 to about 3 Pa·s, about 0.7 to about 2 Pa·s, about 0.8 to about 1.8 Pa·s or about 1 to about 1.8 Pa·s. The viscosity of polymeric solutions in DMSO is measured at 25° C. If not otherwise specified, the viscosity value of the polymeric solution or the injectable composition is given in Pa·s units.

In some embodiments, the weight ratio of DMSO to PLA is about 1:1 to about 2.3:1, about 1.2:1 to about 1.8:1, about 1.3:1 to about 1.5:1, or about 1.4:1.

In some embodiments, the weight ratio of DMSO to drug is in the range of about 0.5 to about 3.7, about 1:1 to about 3:1, about 1.5:1 to about 2:1, about 1.7:1 to about 1.8:1, or about 1.75:1.

In some embodiments, the weight ratio of polymer solution to drug is about 1:1 to about 5.7:1, about, 2.3:1 to 4:1, about 2.8:1 to about 3.2:1, or about 3:1.

In some embodiments, the weight ratio of PLA to drug is about 0.6:1 to about 2.8:1, about 1.0 to 2.0, about 1.1:1 to 1.6:1, about 1.1:1 to about 1.4:1, about 1.1:1 to about 1.35:1, about 1.1:1 to about 1.3:1, about 1.2:1 to about 1.3:1, or about 1.25:1.

In some embodiments, the drug is partially dissolved or completely undissolved in the polymeric solution. In some embodiments, ≤5%, ≤10%, ≤20% wt of the drug is dissolved in the solvent or polymeric solution to form the injectable composition. In some embodiments, >0%, ≥0.5%, ≥1%, ≥5%, or ≥10% wt. of the drug is dissolved in the solvent or polymeric solution to form the injectable composition.

The expression "immediate onset of action" as used herein means that the estrogen plasma level suppression achieved by the composition of the invention is at least as early as the one achieved by oral therapy with FEMARA®, namely at day 4. For example, FEMARA® (oral) and a composition of the invention (Letrozole ISM) were compared by administering a dose of each to human subjects. The results (depicted in FIG. 1) demonstrate that no estradiol (E2) can be detected, meaning E2 is below the detection limit. Importantly, however, a lower dose of letrozole was administered as Letrozole ISM than as FEMARA®. Accordingly, the composition of the invention is able to reduce the plasma level of E2 to less than 1.0 pg/mL, less than 0.8 pg/mL, less than 0.5 pg/mL, less than 0.3 pg/mL, or less than 0.1 pg/mL within about four days after administration and continuously throughout a dosing period.

Figure 2:
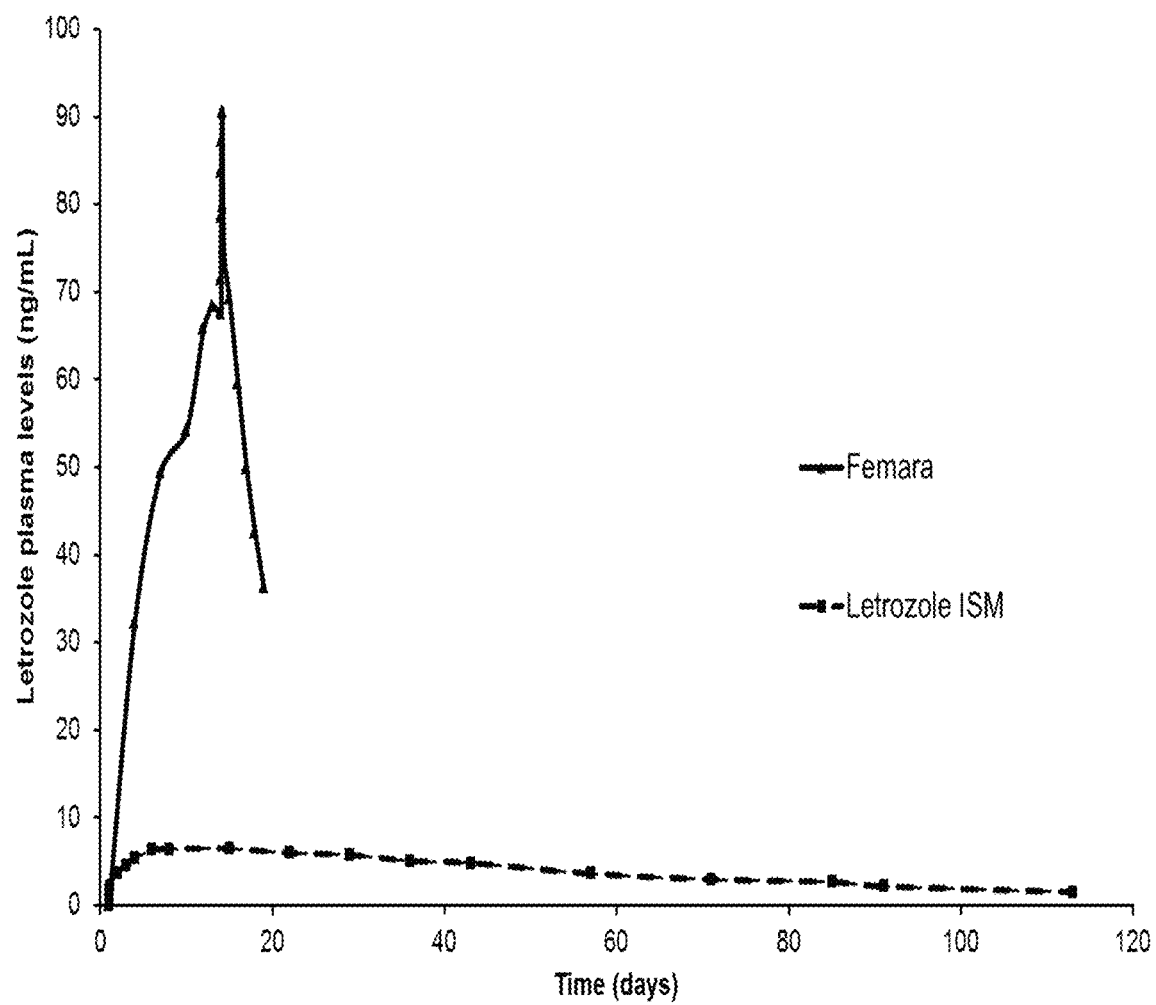

The performance of FEMARA® and a composition of the invention (Letrozole ISM) was compared (FIG. 2) in terms of plasma concentration achieved after administration of a dose to human subject. The FEMARA® composition provided extremely high plasma concentrations of letrozole, which can then be associated with much higher incidence or severity of adverse events. On the other hand, the composition of the invention provided a) no burst release of letrozole; b) substantially longer sustained letrozole plasma levels of letrozole; and c) therapeutically effective plasma levels of letrozole for about 16 weeks (about 4 months) or more.

The relative impact of particle size distribution of PLA was determined by comparing the in vitro dissolution profile (drug release profile) for various extended release compositions formed from injectable depot compositions comprising PLA of different particle size distributions.

Figure 3:
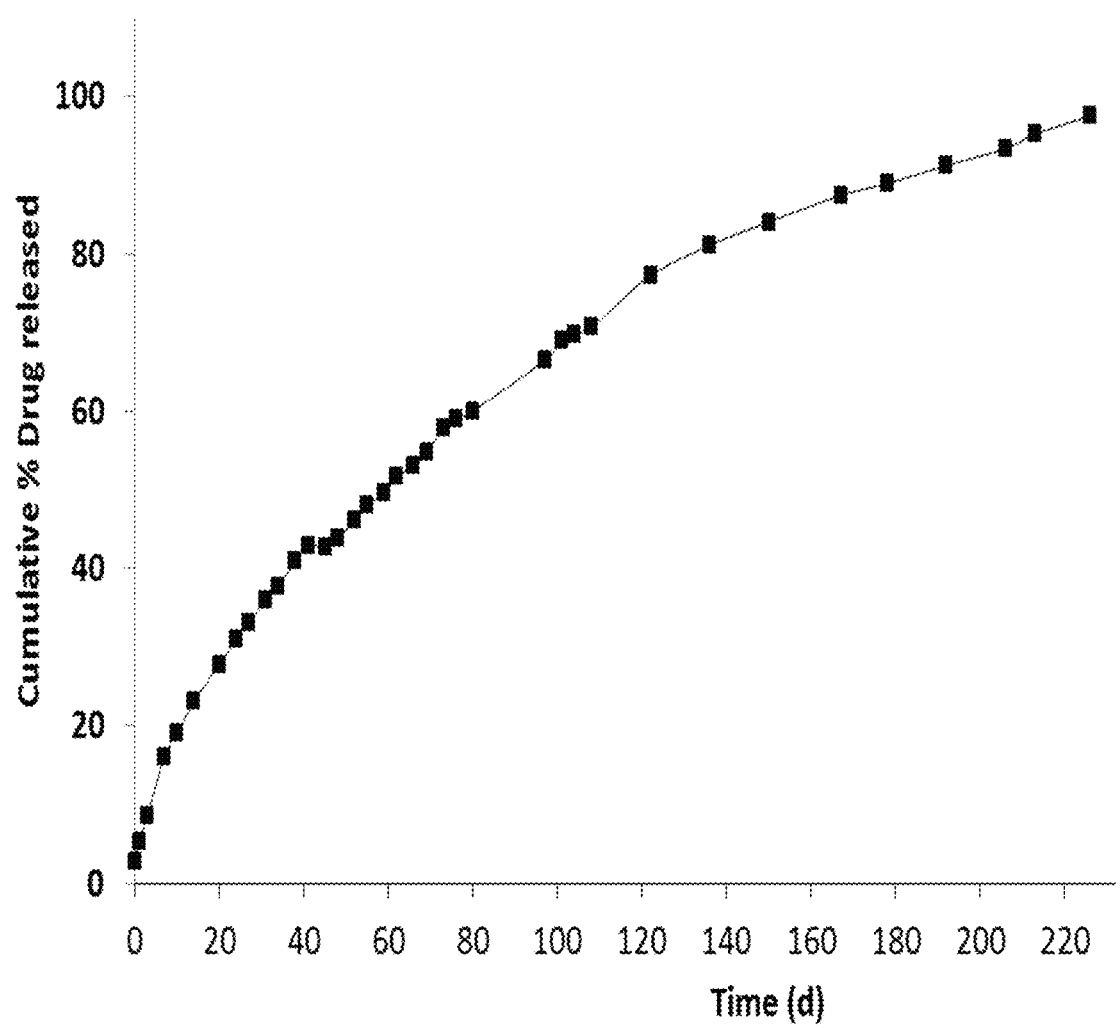
FIG. 3 depicts a chart of cumulative percentage of released letrozole versus time (d) in an in vitro dissolution test from a composition comprising PLA having a particle size mass distribution where more than 10% of the particles have a particle size of 300 microns or more, when measured by analytical sieving according to USP<786>.

The impact of the relative content of larger PLA particles was determined. FIG. 3 depicts a chart of cumulative percentage of released letrozole versus time (d) in an in vitro dissolution test from a composition (not according to the invention) comprising PLA having a particle size mass distribution where more than 10% of the particles have a particle size of 300 microns or more, when measured by analytical sieving according to USP<786>. The PLA used in the composition of FIG. 3 had a particle size mass distribution where 18.1% of the particles were bigger than 300 microns and 28.3% of the particles were smaller than 125 microns, measured by analytical sieving according to USP<786>. Said PLA had a particle size volume distribution with a D90 of 421 microns and a D80 of 324 microns when measured by laser diffraction analysis.

Figure 4:
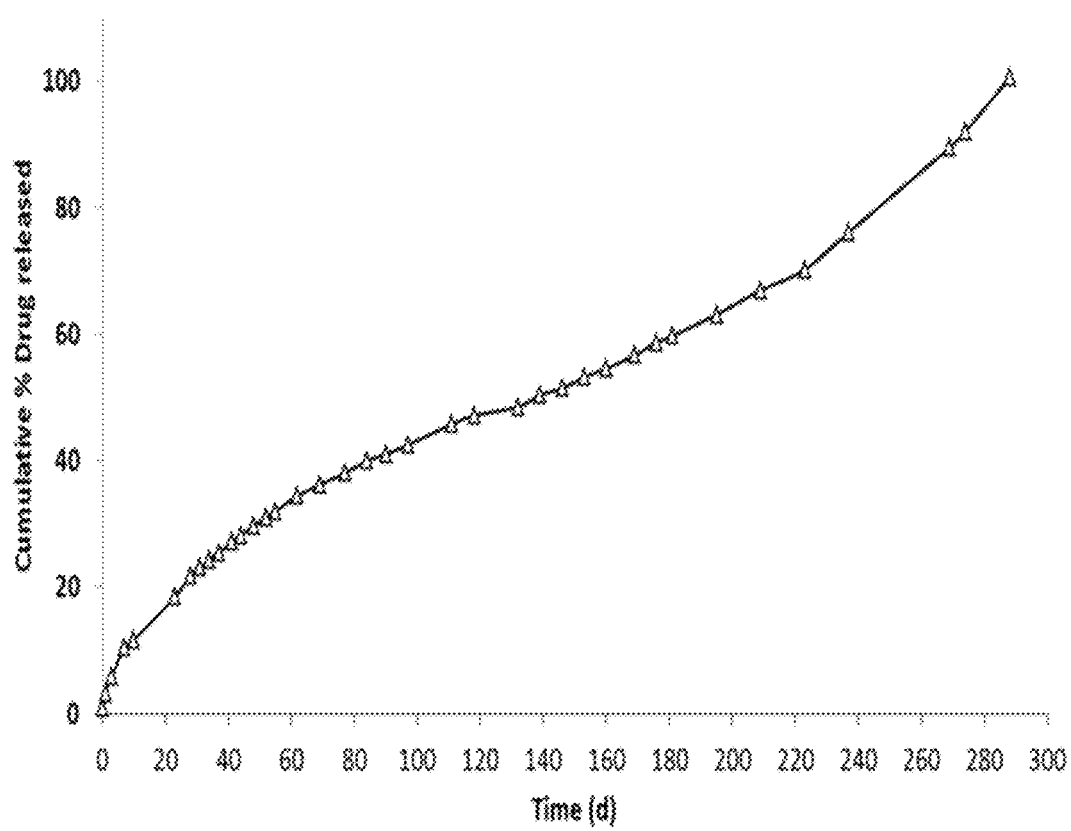
FIG. 4 depicts a chart of cumulative percentage of released letrozole versus time from a composition of the invention in an in vitro dissolution test.

FIG. 4 depicts a chart of cumulative percentage of released letrozole versus time from a composition of the invention in an in vitro dissolution test. The PLA used had a particle size mass distribution where 0.8% of the particles were bigger than 300 microns and 58.5% of the particles were smaller than 125 microns, measured by analytical sieving according to USP<786>. Said PLA had a particle size volume distribution with a D90 of 214 microns and a D80 of 170 microns when measured by laser diffraction analysis. The sustained release was satisfactory and was unexpectedly about two months longer than that provided by the PLA not according to the invention (FIG. 3).

Figure 5:
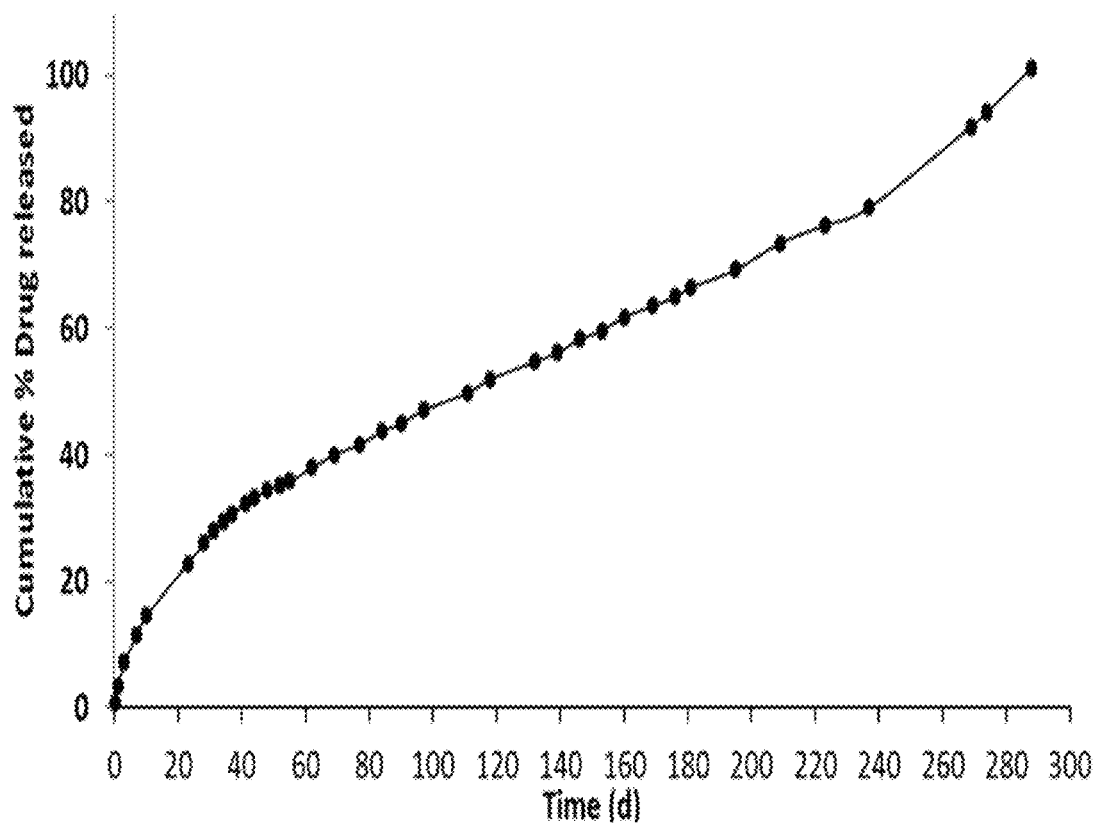
FIG. 5 depicts a chart of cumulative percentage of released letrozole versus in an in vitro dissolution test from a composition comprising PLA having a particle size mass distribution wherein at least 80% of the particles have a particle size of 125 microns or less, when measured by analytical sieving according to USP<786>.

The impact, upon drug dissolution, of the relative content of smaller PLA particles was determined. FIG. 5 depicts a chart of cumulative percentage of released letrozole versus in an in vitro dissolution test from a composition comprising PLA having a particle size mass distribution wherein at least 80% of the particles have a particle size of 125 microns or less, when measured by analytical sieving according to USP<786>. The PLA used in the composition had a particle size mass distribution where 1.6% of the particles were bigger than 300 microns and 88.8% of the particles were smaller than 125 microns, measured by analytical sieving according to USP<786>. Said PLA had a particle size volume distribution with a D90 of 155 microns and a D80 of 124 microns when measured by laser diffraction analysis. The implant provided satisfactory sustained release results; even though, it formed hard agglomerates during initial mixing of the DMSO, PLA and drug.

Figure 6A:
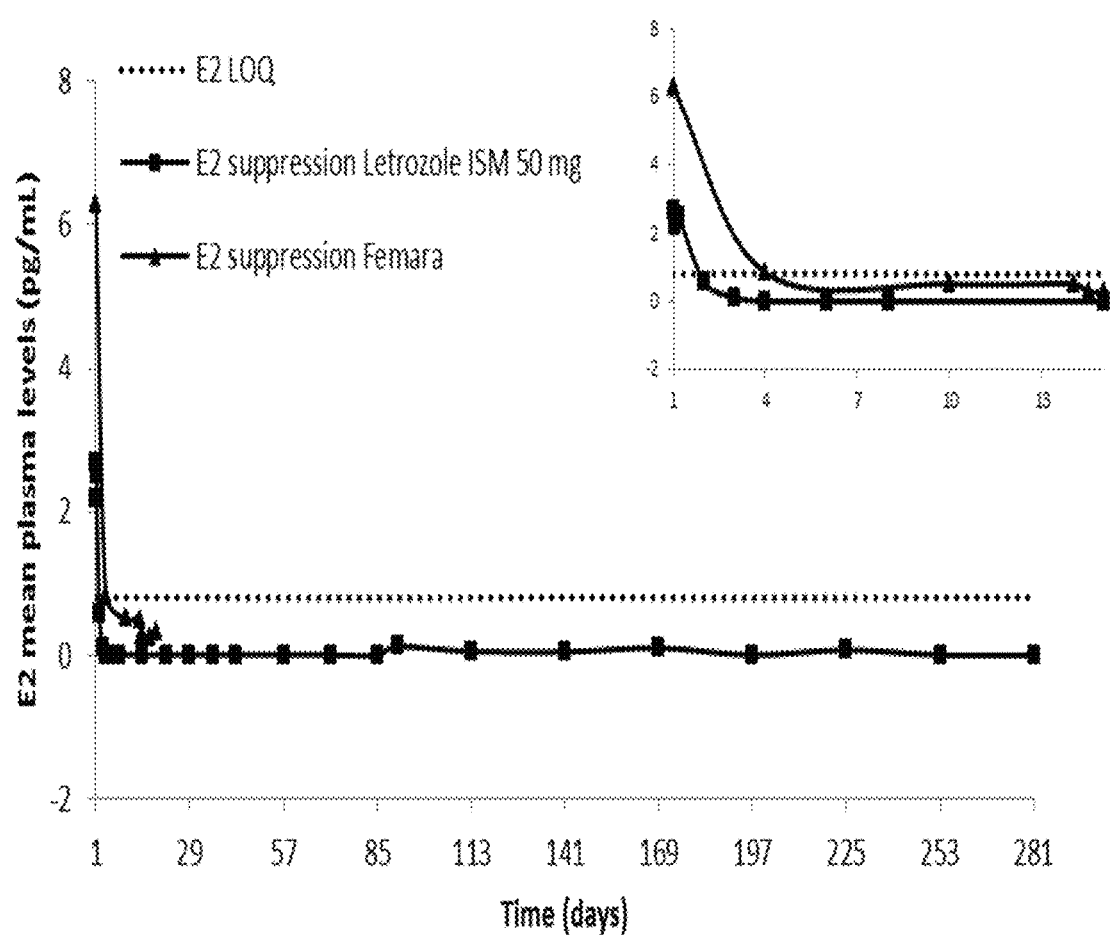
FIGS. 6A and 6B depict chart of estradiol (E2) plasma levels (pg/ml) observed versus time after administration of FEMARA® or the composition of the invention (Letrozole ISM comprising 50 mg of letrozole). The inset depicts an expanded view of the first 15 days.
Figure 6B:
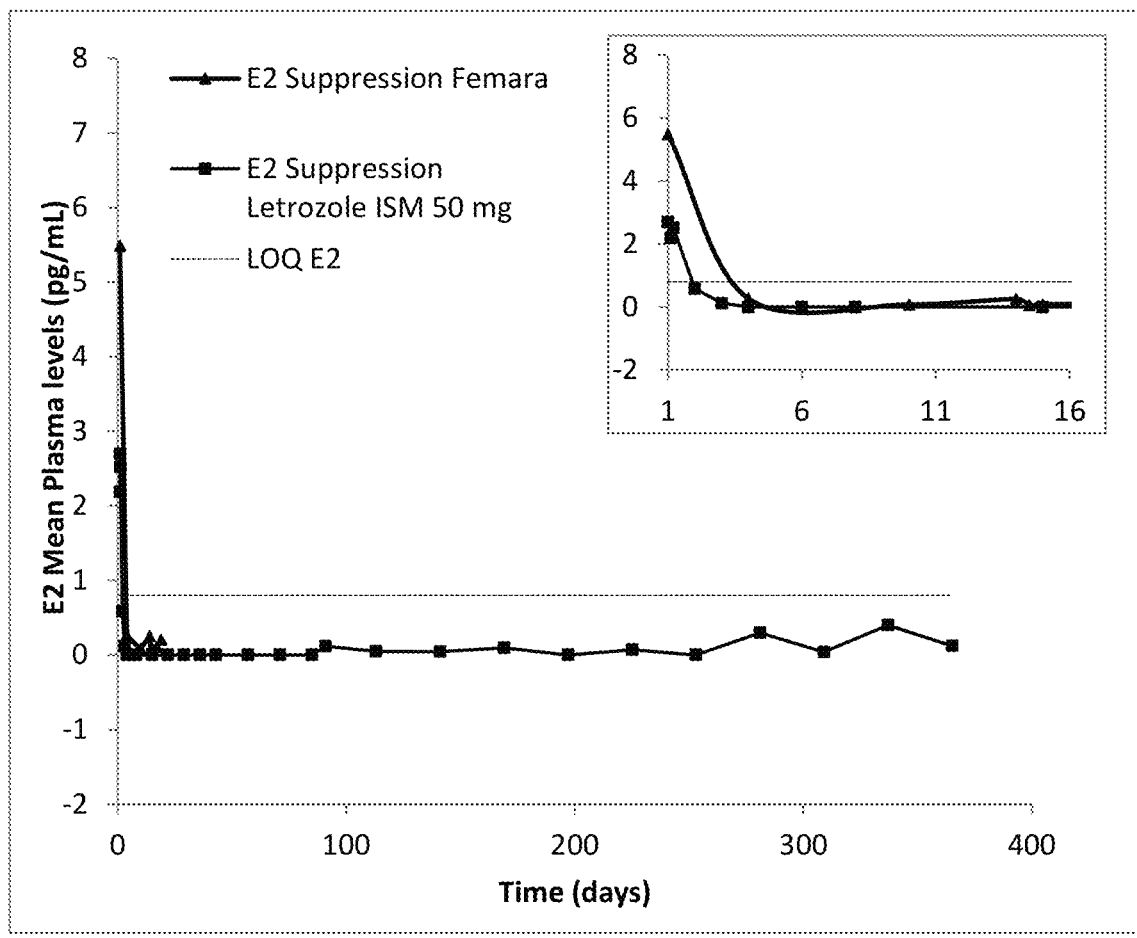
Figure 7A:
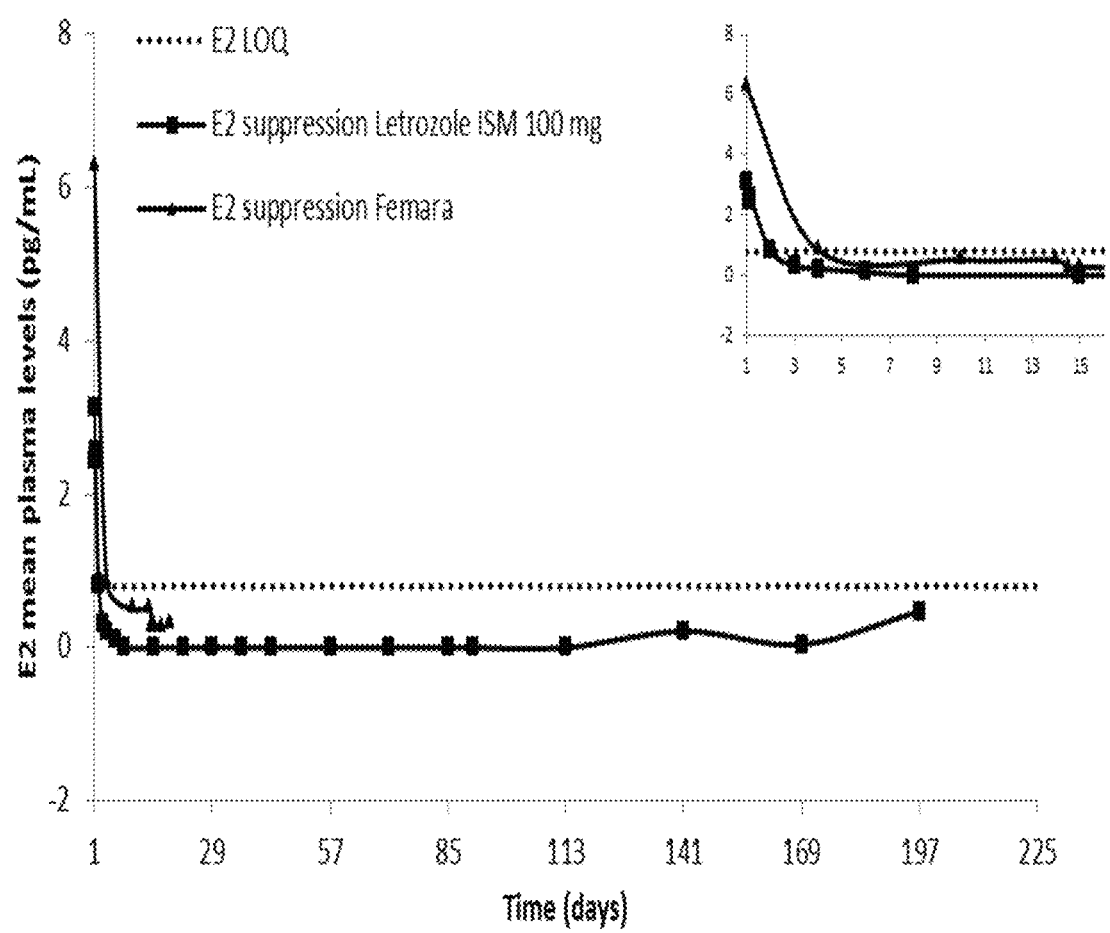
FIGS. 7A and 7B depict charts of estradiol (E2) plasma levels (pg/ml) observed versus time after administration of FEMARA® or the composition of the invention (Letrozole ISM comprising 100 mg of letrozole). The inset depicts an expanded view of the first 15 days.
Figure 7B:
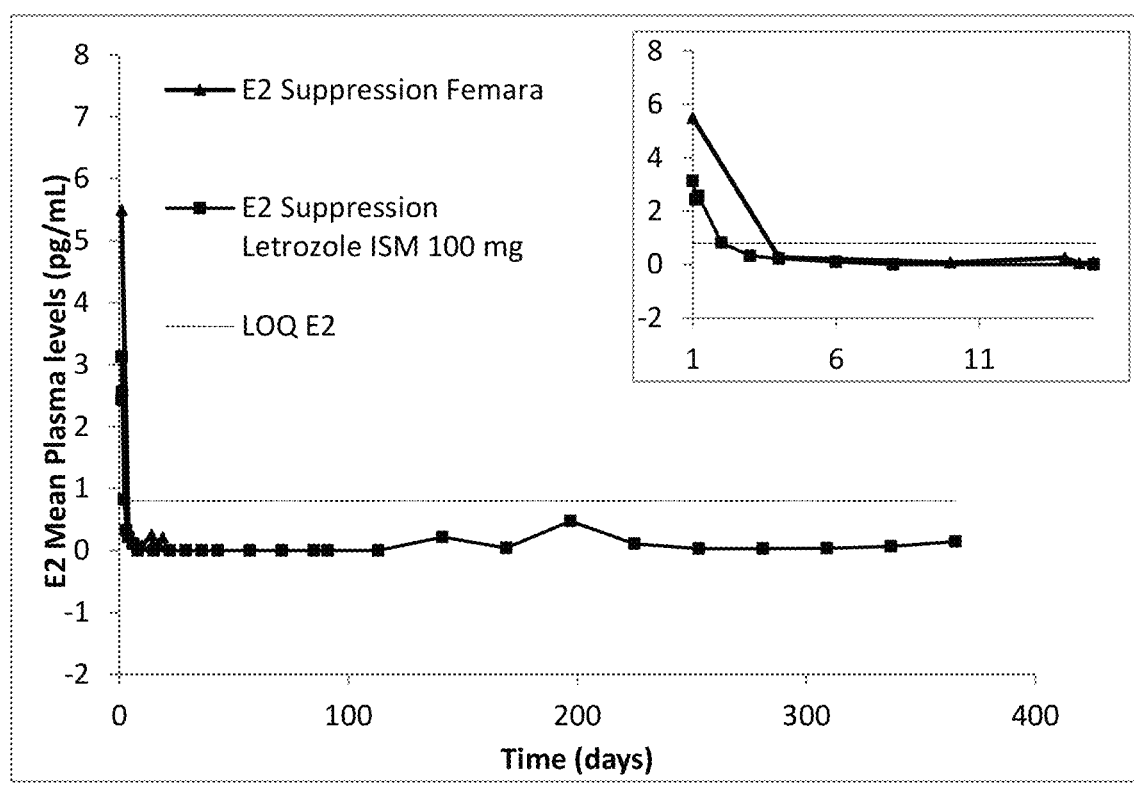

FIGS. 6A and 6B depict chart of estradiol (E2) plasma levels (pg/ml) observed versus time after oral administration of FEMARA® (2.5 mg once daily for 14 days) or intramuscular administration of the composition of the invention (Letrozole ISM; one injection comprising 50 mg of letrozole) according to Example 3 (Cohort 1). The inset depicts an expanded view of the first 15 days. FIGS. 7A and 7B depict charts of estradiol (E2) plasma levels (pg/ml) observed versus time after oral administration of FEMARA® (2.5 mg once daily for 14 days) or intramuscular administration of the composition of the invention (Letrozole ISM; one injection comprising 100 mg of letrozole) according to Example 3 (Cohort 2). The inset depicts an expanded view of the first 15 days. Plasma estrogen levels decreased rapidly from baseline following administration of letrozole. The hormones decreased to stable levels below 1 pg/mL at approximately 4 days post-Femara®/Letrozole ISM treatment (FIGS. 6A, 6b, 7A and 7B). The sustained suppression of estrogen levels was maintained for at least about 365 days (or at least about 6 months, at least about 9 months, at least about 10 months, at least about 11 months, or at least about 12 months) for Letrozole ISM 50 mg and 100 mg. There were no apparent differences in the extent of hormonal level decrease between Letrozole ISM 50 mg and 100 mg. It is very surprising that a 50 mg dose injectable composition was as effective as a 100 mg dose injectable composition in terms of E2 suppression.

Figure 8:
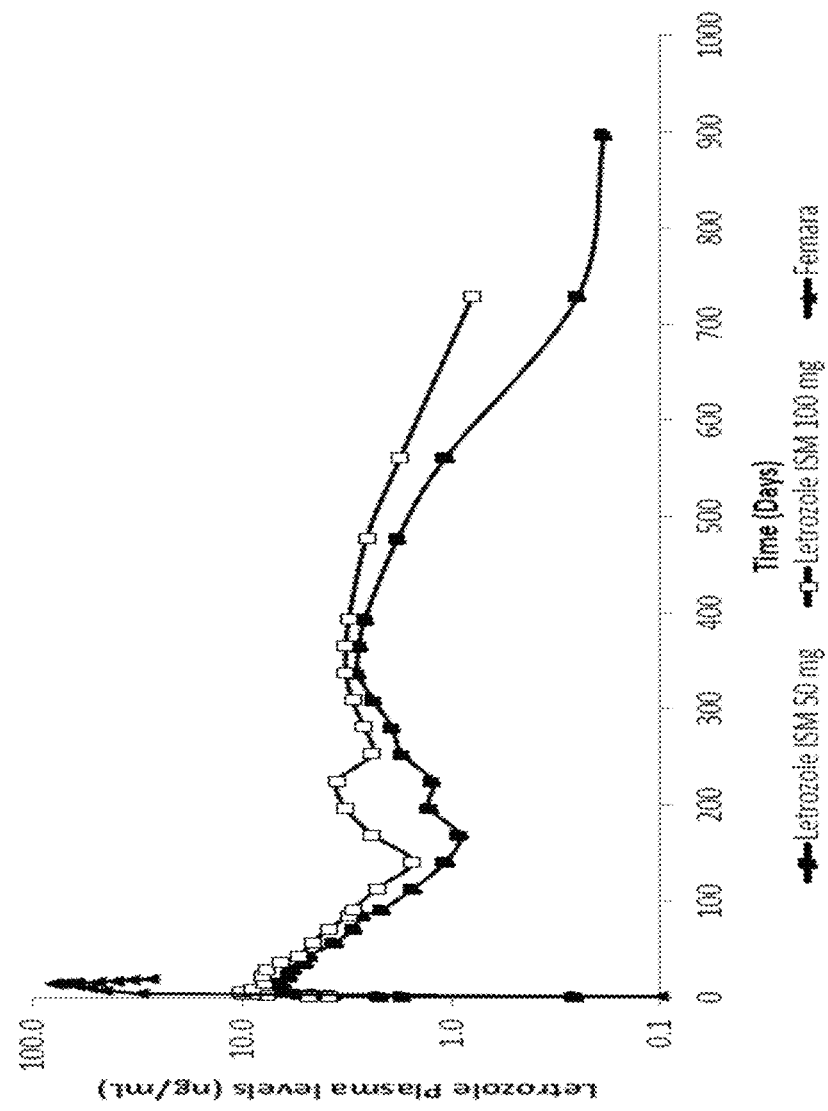
FIG. 8 depicts a chart of letrozole plasma levels (ng/ml) observed versus time after administration of FEMARA® or the compositions of the invention (Letrozole ISM 50 mg or 100 mg).
Figure 9:
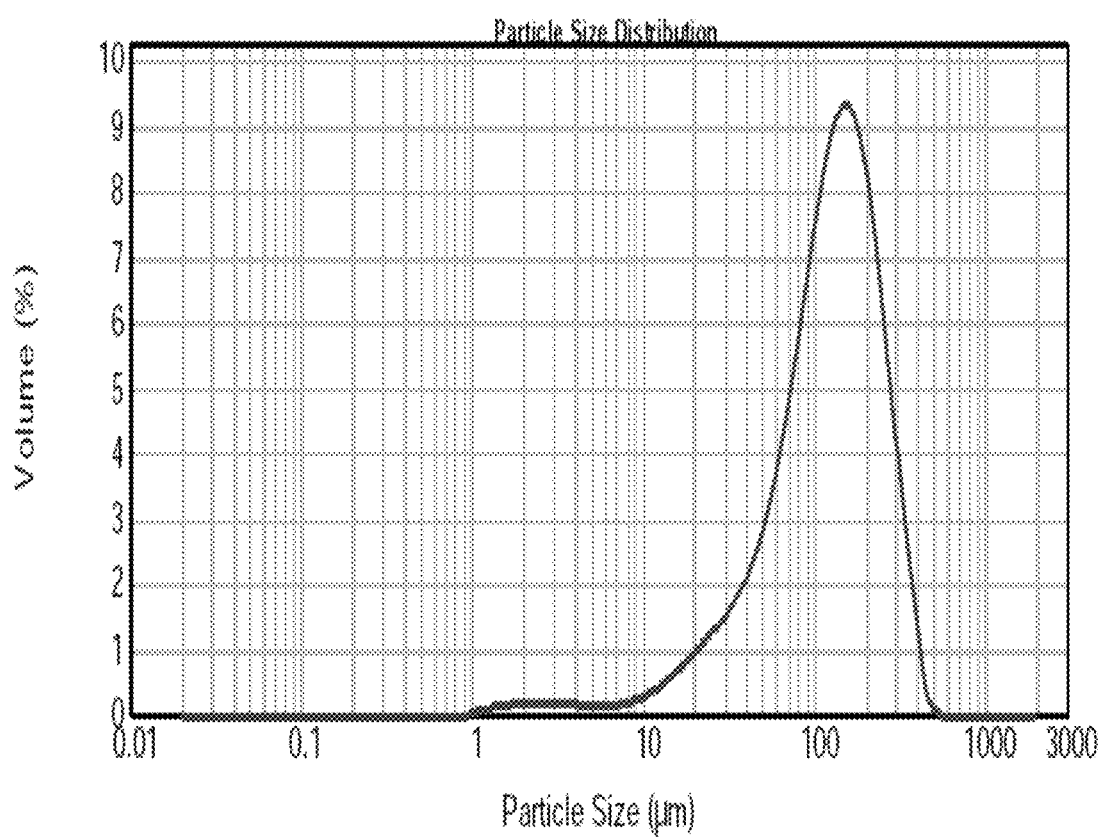
FIG. 9 depicts a chart of the particle size distribution of an exemplary PLA of the composition of the invention measured by laser diffraction analysis (Horizontal axis: particle size in microns; Vertical axis: volume (%), indicating the percentage of particles with the corresponding particle size, measured by laser diffraction by wet dispersion method in water and dispersing by stirring at 3000 rpm).

FIG. 8 depicts a chart of letrozole plasma levels (ng/ml) observed versus time after administration of FEMARA® (2.5 mg once daily for 14 days) or the compositions of the invention (Letrozole ISM 50 mg or 100 mg) corresponding to FIGS. 6 and 7. Letrozole mean maximum exposure concentrations observed for FEMARA® at steady state (2.5 mg QD for 14 days) were approximately 12-fold and 8-fold greater than that observed for Letrozole 50 mg and 100 mg doses, respectively. The much higher plasma concentration provided by FEMARA® would provide corresponding higher severity and/or incidence of adverse events as compared to the much lower and still therapeutically effective plasma concentration provided by the composition(s) of the invention.

By overlaying the charts of FIGS. 6A, 6B, 7A, and 7B, the 100 mg injectable composition has twice the dose of letrozole as the 50 mg injectable composition, both compositions are effective at maintaining the plasma levels of E1 (estrone) and E2 (estradiol) below the LOQ, the level of quantitation, for at least about 365 days.

Accordingly, the composition(s) of the invention provide(s) therapeutically effective plasma levels of letrozole for at least 6 months, at least 7 months, at least 8 months, at least 9 months, at least 10 months, at least 11 months, or at least 12 months, while concomitantly providing reduced adverse events.

The invention provides a method of treating a disease, disorder or condition that is therapeutically responsive to nonsteroidal inhibitor of aromatase. Said nonsteroidal inhibitor can be letrozole, anastrozole, or metabolite of either thereof. Exemplary diseases, disorders or conditions include, for example: a) adjuvant treatment (treatment following surgery with or without radiation) of postmenopausal women with hormone receptor-positive early breast cancer; b) metastasis in both pre and post-menopausal women; c) precocious puberty or children with pubertal gynecomastia; d) reducing estrogens, including estradiol, in men; e) hormonally-responsive breast cancer after surgery; f) ovarian stimulation; g) promote spermatogenesis in male patients suffering from nonobstructive azoospermia; h) endometriosis; i) cancer that is estrogen hormone receptor-positive or sensitive (non-small cell lung cancer, uterine leiomyomas, etc.); j) infertility in women with polycystic ovarian syndrome; k) ovarian cancer; l) breast cancer that is estrogen hormone receptor positive or sensitive; j) priming for in vitro maturation cycles; k) preoperative treatment with letrozole in premenopausal women undergoing laparoscopic myomectomy of large uterine myomas; l) short stature in peripubertal boys; m) unexplained infertility or infertility with unknown or uncertain etiology; n) idiopathic central precocious puberty in boys.

The invention also provides a method of forming an injectable depot composition, the method comprising mixing solvent, PLA polymer and drug to form the injectable depot composition as defined herein. The solvent, PLA and drug may be in one, two, three or more containers. In one embodiment, PLA and drug are in a container and solvent is in a separate container and the contents of the containers are mixed to form the composition. In another embodiment, PLA, drug, and solvent are in separate containers, and the contents of the containers are mixed to form the composition. In another embodiment, PLA and solvent are in a container, and drug is in a separate container, and the contents of the containers are mixed to form the composition. The container(s) may be part of a pharmaceutical kit. Accordingly, the invention also provides a pharmaceutical kit comprising the one or more containers, wherein the content of the container(s) are as described herein.

The invention provides a method administering letrozole or anastrozole to a subject. The method comprises administering an amount (or volume) of injectable composition comprising the aromatase inhibitor. The method may further comprise the step of forming the injectable composition before administration thereof. The method may further comprise the step of providing a kit comprising containers with the ingredients of the injectable composition. The composition can be administered every about 30 days, about 45 days, about 60 days, about 90 days, about 120 days, or 150 days, or about every month, about every two months, about every three months, about every four months, about every five months, about every six months, about every nine months, about every ten months, about every eleven months, about every twelve months, or as often as needed for as many times needed to ameliorate the disease, disorder or condition. Combinations of the dosing regimens herein are contemplated. The composition provides therapeutic plasma levels for a period of at least 1 month, at least 2 months, at least 3 months, at least 4 months, at least 5 months, at least 6 months, at least 9 months, at least 10 months, at least 11 months, or at least twelve months following administration of a dose of said composition.

The injectable composition can be administered to muscle tissue, adipose tissue, peritoneum, or below the skin. Intramuscular administration is preferred. In some embodiments, the composition is administered to the gluteal and/or deltoid muscles. The composition can also be administered to the quadriceps muscle group. A dose can be administered to a single muscular site or can be divided into two or more portions and administered to two or more muscular sites of a subject. For example, a first portion of a dose can be administered to a first section of gluteal muscle and a second portion of the dose can be administered to a second section of gluteal muscle of a subject. A single-body implant will form at each injection site. Such a mode of administration within a same day is considered to be administration of a single dose with a single dosing period. Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

A dose of the injectable composition typical comprises about 30 to about 90 mg of letrozole, about 80 to about 150 mg of letrozole, about 150 to about 250 mg of letrozole, about 250 to about 350 mg of letrozole, about 350 to about 450 mg of letrozole, about 20 to about 500 mg of letrozole, about 50 mg of letrozole, about 100 mg of letrozole, about 200 mg of letrozole, or about 400 mg of letrozole.

Following administration to a subject, the composition will form one or more implants (preferably a single implant) in said subject.

Administration of a single dose is typically considered that amount of injectable composition administered to a subject within a period of up to 24 hours, up to 12 hours, up to 6 hours, up to 3 hours, up to one hour, up to 30 min, up to 15 min or up to 5 min.

In another embodiment, the injectable depot composition is sterile as a finished product. In another embodiment, the biocompatible polymer is sterilized previously to its aseptic filling process, preferably by irradiation (such as beta irradiation) or by another process, e.g. filtration.

The implant of the invention can provide substantially improved plasma levels of drug when compared to another injectable formulation (not according to the invention) containing the same drug when administered on an equivalent dose basis.

The invention also provides an implant comprising PLA and drug (which is letrozole, anastrozole, or salt of either thereof, or metabolite of either thereof), wherein a) the weight ratio of PLA to drug is about 0.6:1 to about 2.8:1, about 1.0 to 2.0, about 1.1:1 to 1.6:1, about 1.1:1 to about 1.4:1, about 1.1:1 to about 1.35:1, about 1.1:1 to about 1.3:1, about 1.2:1 to about 1.3:1, or about 1.25:1; b) the implant has been prepared from a composition comprising i) 15-35 wt. % letrozole, 25-35 wt. % PLA, and 30-60 wt. % DMSO; ii) 18-28 wt. % letrozole, 30-35 wt. % PLA, and 37-52 wt. % DMSO; iii) about 23 to about 27 wt. % letrozole, about 28 to about 34 wt. % PLA, and about 41 to about 47 wt. % DMSO; or iv) about 24 to about 26 wt. % letrozole, about 29 to about 33 wt. % PLA, and about 42 to about 47 wt. % DMSO, wherein the weight percentages are with respect to the total weight of the composition before formation of the implant. When administered to a subject, the implant releases from about 0.1 to about 2 milligrams of letrozole daily and provides a plasma level of letrozole between about 1 to about 40 ng/ml from about 2 days after administration and continuously throughout a dosing period. Prior to formation of the implant, the particle size distribution of the PLA in the composition is as defined herein according to the invention. The PLA is optionally sized before being included in the composition. The implant may be used in a method of administering or a method of treating as defined herein.

The invention also provides a method of forming an implant, the method comprising a) mixing DMSO, PLA and drug to form an injectable depot composition; and b) administering the injectable depot composition to a subject. The content and characteristics/properties of the ingredients are as defined herein. The particle size distribution of the PLA, prior to implant formation, is as defined herein. The in vivo and in vitro performance of the implant is as defined herein.

All values disclosed herein may have standard technical measure error (standard deviation) of ±10%. The term "about" is intended to mean±10%, ±5%, ±2.5% or ±1% relative to a specified value, i.e. "about 20%" means 20±2%, 20±1%, 20±0.5% or 20±0.25%

EXAMPLES

The following examples are illustrative of the invention and are not to be considered limiting.

Example 1

Compositions

The following formulations are prepared.

A ready-to-use formulation can be prepared, for example, and included in a syringe ready for use for intramuscular injection. The same formulation may form part, for example, of a kit of two syringes, one male and one female or two male syringes linked by a connector in which the solution of PLA in DMSO is in one syringe and the letrozole is in solid form in a second syringe. Similarly, the final composition can be obtained by, for example, maintaining one syringe with the PLA and letrozole in solid state and the solvent (DMSO) in a second syringe.

Formulation 1:

| Ingredient | Amount (mg, % wt) |
|---|---|
| Lactic acid polymer (ester terminal group) of intrinsic viscosity of 0.3 dl/g, irradiated as raw material at 10 kGy. | 55.20 (35.8%) |
| Dimethyl sulfoxide | 82.80 (53.7%) |
| Letrozole | 16.20 (10.5%) |

The weight ratio of DMSO to PLA is about 1.5:1. The weight ratio of DMSO to drug is about 5.11:1. The weight ratio of polymeric solution to drug is about 8.52:1. The weight ratio of PLA to drug is about 3.41:1.

Formulation 2: Formulation with Letrozole in Suspension

| Ingredient | Amount (mg, % wt) |
|---|---|
| Lactic acid polymer (ester terminal group) of intrinsic viscosity of 0.3 dl/g, irradiated as raw material at 10 kGy. | 38.80 (30%) |
| Dimethyl sulfoxide | 58.30 (45%) |
| Letrozole | 32.40 (25%) |

Letrozole particle size in formulation 2 was characterized by the technique of laser ray diffraction (Malvern Mastersizer 2000, suspended in water until obscuration of 9.41%) and had the following distribution (in % volume): d(0.1)=38.21 µm, d(0.5)=141.35 µm and d(0.9)=312.13 µm.

The weight ratio of DMSO to PLA is about 1.5:1. The weight ratio of DMSO to drug is about 1.8:1. The weight ratio of polymeric solution to drug is about 3:1. The weight ratio of PLA to drug is about 1.2:1.

Formulation 3:

| Ingredient | Amount (mg) |
|---|---|
| Lactic acid polymer (carboxylic terminal group) of intrinsic viscosity of 0.3 dl/g, irradiated as raw material at 10 kGy. | 38.80 |
| Dimethyl sulfoxide | 58.30 |
| Letrozole | 32.40 |

The weight ratio of DMSO to PLA is about 1.5:1. The weight ratio of DMSO to drug is about 1.8:1. The weight ratio of polymeric solution to drug is about 3:1. The weight ratio of PLA to drug is about 1.2:1.

Formulation 4:

| Ingredient | Amount (mg) |
|---|---|
| Lactic acid polymer (ester terminal group) of intrinsic viscosity of 0.3 dl/g, irradiated as raw material at 10 kGy. | 38.80 |
| Dimethyl sulfoxide | 58.30 |
| Letrozole | 32.40 |

The weight ratio of DMSO to PLA is about 1.5:1. The weight ratio of DMSO to drug is about 1.8:1. The weight ratio of polymeric solution to drug is about 3:1. The weight ratio of PLA to drug is about 1.2:1.

Formulation 5:

| Ingredient | Amount (mg, % wt) |
|---|---|
| Lactic acid polymer (carboxylic terminal group) of intrinsic viscosity of 0.3 dl/g, irradiated as raw material at 10 kGy. | 107.6 (31.1%) |
| Dimethyl sulfoxide | 151.7 (43.9%) |
| Letrozole | 86.5 (25%) |

The weight ratio of DMSO to PLA is about 1.41:1. The weight ratio of DMSO to drug is about 1.75:1. The weight ratio of polymeric solution to drug is about 3:1. The weight ratio of PLA to drug is about 1.25:1.

Formulation 6:

| Ingredient | Amount (mg) |
|---|---|
| Lactic acid polymer (ester terminal group) of intrinsic viscosity of 0.3 dl/g, irradiated as raw material at 10 kGy. | 107.6 |
| Dimethyl sulfoxide | 151.7 |
| Letrozole | 86.5 |

The weight ratio of DMSO to PLA is about 1.41:1. The weight ratio of DMSO to drug is about 1.75:1. The weight ratio of polymeric solution to drug is about 3:1. The weight ratio of PLA to drug is about 1.25:1.

Formulations 7 to 12:

| Formulation Ingredient | 7 Amount (% wt) | 8 Amount (% wt) | 9 Amount (% wt) | 10 Amount (% wt) | 11 Amount (% wt) | 12 Amount (% wt) |
|---|---|---|---|---|---|---|
| Lactic acid polymer (PLA) terminating in a carboxylic group | 28-36 | 15-42.5 | 29.6-32.7 | | | |
| Lactic acid polymer (PLA) ester terminal group | | | | 15-42.5 | 28-36 | 29.6-32.7 |
| Dimethyl sulfoxide | 38.5-52 | 25-59.5 | 42.2-45.6 | 25-59.5 | 38.5-52 | 42.2-45.6 |
| Letrozole | 20-30 | 15-50 | 24-26 | 15-50 | 20-30 | 24-26 |

For some preferred compositions, the % w/w in the composition of the active agent was between 20.0 and 27.0%. The % w/w in the composition of the PLA was between 20.0 and 50.0%. The % w/w in the composition of the solvent was between 23.0 and 60.0%. The compositions were mixed in a syringe to form suitable implants.

Different types of PLA were used for these compositions:
1. PLA with particle size mass distribution where more than 10% of the particles had a particle size of 300 microns or above when measured by analytical sieving according to USP<786>;
2. PLA with particle size volume distribution with D90 above 330 microns when measured by laser diffraction analysis;
3. PLA with particle size mass distribution where no more than 10% of the particles had a particle size above 300 microns and no more than 80% of the particles have a particle size below 125 microns when measured by analytical sieving according to USP<786>;
4. PLA with particle size volume distribution with D90 not above 330 microns and D80 not below 135 microns when measured by laser diffraction analysis;
5. PLA with particle size mass distribution where more than 80% of the particles have a particle size below 125 microns, when measured by analytical sieving according to USP<786>;
6. PLA with particle size volume distribution with D80 below 135 microns when measured by laser diffraction analysis.

Compositions of the invention were prepared first by dry mixing the active agent with the PLA and then adding the solvent, preferably DMSO to dissolve the PLA and have a suspension of the active agent. The reconstitution process is to be carried out immediately prior to injection, and the time for preparation does not exceed 15 minutes, preferably 10 minutes, more preferably 5 minutes, before the IM composition is administered.

The implants prepared this way were used for the following dissolution test: horizontal orbital motion at 50 rpm; medium: PBS pH 7.4.; temperature: 37±0.5° C.; analytical technique HPLC/UV; wavelength 230 nm.

It was observed that for PLAs 1 and 2, the release was not as satisfactory sustained as desired when preferred time of preparation was applied (FIG. 3). However, for PLAs 3 and 4, the sustained release was satisfactory (FIG. 4).

When PLAs 5 and 6 were used, big and hard agglomerates formed, and the composition could not be prepared within the preferred time of no more than 15 minutes. Thus, this composition was not considered clinically suitable. In any case, the implant was assayed, and sustained release resulted satisfactory (FIG. 5).

Example 2

Particle Size Determination

Analytical Sieving According to USP<786>

The PLA particle size mass distribution was determined by sieve stack technique using the following sizes: 425>355>300>250>212>180>150>125>106>75. The amplitude was 0.65 mm and the shaking time 5 minutes.

Laser Light Diffraction

The PLA particle size distribution is expressed as volume distribution and was determined by laser diffraction technique by wet dispersion method. No sample pre-treatment was applied. The sample was directly added into the dispersion medium (water). Dispersion mechanism was stirring at 3000 rpm and the sample was stabilized for 30 seconds before measuring.

Example 3

Clinical Data

Preliminary Phase I Results

Preliminary results suggest that sustained long-term hormone suppression therapy (HT) may obtain a superior clinical outcome in breast cancer compared to an oral daily dosage treatment.

Early discontinuation and non-adherence to HT are common and associated with increased mortality—improved treatment compliance with Letrozole ISM® has potential to enhance treatment.

Sustained lower effective doses (compared to oral treatment) could reduce adverse side effects (bone mass loss, bone/joint/muscle pain, dyslipidemia) due to lower exposure to drug.

Better safety profile has potential to positively impact treatment duration adherence.

Phase I Results

This is a Phase I, open label, dose escalation study designed to evaluate the pharmacokinetics, safety, and tolerability of single intramuscular injections of Letrozole ISM at different strengths in approximately 120 voluntary healthy postmenopausal women. The study has four arms:

Experimental: Cohort 1: Letrozole ISM 50 mg: 14 oral doses of 2.5 mg FEMARA® (once daily)+single IM injection of 50 mg Letrozole ISM.

Experimental: Cohort 2: Letrozole ISM 100 mg: 14 oral doses of 2.5 mg FEMARA® (once daily)+single IM injection of 100 mg Letrozole ISM.

Experimental: Cohort 3: Letrozole ISM 200 mg: 14 oral doses of 2.5 mg FEMARA® (once daily)+single IM injection of 200 mg Letrozole ISM.

Experimental: Cohort 4: Letrozole ISM 400 mg: 14 oral doses of 2.5 mg FEMARA® (once daily)+single IM injection of 400 mg Letrozole ISM.

The objective of this study is to assess the pharmacokinetic profile of a single ascending doses of Letrozole ISM, and secondly, to evaluate safety and tolerability of single ascending doses of Letrozole ISM, measure estrogen levels, and characterize oral letrozole pharmacokinetic profile to be used in subsequent comparison to Letrozole ISM.

The study is carried out in healthy post-menopausal women who satisfy inclusion and exclusion criteria. The study design includes a screening period and 2 treatment periods. Treatment Period 1 comprises of 14 oral dose administrations of 2.5 mg Femara®. Treatment Period 2 comprises of a single IM dose of 50, 100, 200 and 400 mg Letrozole ISM. The total planned study duration is 71 weeks, approximately.

Inclusion Criteria:

The inclusion/exclusion criteria for the 120 participants are the following:

Healthy post-menopausal women, 18 and 75 years of age, who have achieved complete menopause, either natural or surgical, and amenorrhea, and have not been on hormone replacement therapy in the last 3 months.

Post-menopausal subjects should have absence of menses for 1 year, and oophorectomized subjects should have absence of menses for at least 6 weeks. For oophorectomized subjects and subjects who have had a hysterectomy, a surgical pathology report documenting the absence of malignant disease is required. In addition, for oophorectomized subjects an operative report documenting bilateral oophorectomy is required.

Baseline follicle-stimulating hormone (FSH) and 17β-estradiol plasma levels should be consistent with the post-menopausal status of the subject (FSH≥40 mIU/mL; 17β-estradiol≤31 pg/mL), confirmed at least 48 hours prior to dosing.

Weight of ≥50 kg and a BMI≥19 and ≤39 kg/m2.

Subjects will be in good health, as determined by medical history, physical examination, vital signs assessments (pulse rate, systolic and diastolic blood pressure, and temperature), clinical laboratory evaluations, and 12-lead ECG. Minor deviations outside the reference ranges will be acceptable, if deemed not clinically significant by the investigator.

Subjects who have not had a mammogram within the last 12 months (documentation required) must be willing to have one performed.

Subjects with an intact uterus and cervix who have not had a Papanicolaou (pap) smear test within the last 6 months (documentation required) must be willing to have one performed.

Subjects will have given their written informed consent to participate in the study and to abide by the study restrictions.

Subjects should be able to communicate with clinic staff.

Exclusion Criteria:
  Subjects who have a history of allergy or hypersensitivity to letrozole or any of the inactive ingredients in the last 3 months.
  Subjects who have a history of galactose intolerance, severe hereditary lactase deficiency glucose-galactose malabsorption.
  Subjects who have used estrogen or progesterone hormone replacement therapy, thyroid replacement therapy, oral contraceptives, androgens, luteinizing hormone (LH) releasing hormone analogs, prolactin inhibitors, or antiandrogens within 3 months prior to Screening.
  Subjects who have regularly taken foods or food supplements that contain high levels of Isoflavinoids, including soybean, soymilk, soynuts, chickpeas, alfalfa, fava beans, kudzu, miso and tofu in the 14 days prior to dosing (Treatment Period 1). The investigator and medical monitor will determine on a case-by-case basis if a subject who intakes food or food supplements containing Isoflavinoids is eligible to participate in the study.
  Subjects who have used:
    Any medications including St. John's wort, known to be potent or moderate inducers of CYP P450 3A4 in the 3 weeks prior to dosing (Treatment Period 1).
    Any medications or products known to be potent or moderate inhibitors of CYP P450 3A4 (e.g. grapefruit juice) in the 7 days prior to dosing on Treatment Period 1.
    Any prescribed preparations within 14 days prior to dosing (Treatment Period 1), unless in the opinion of the investigator (or designee) the medication will not interfere with the study procedures or compromise safety.
    Any non-prescribed systemic or topical medications within 7 days of dosing (Treatment Period 1) unless in the opinion of the investigator (or designee) the medication will not interfere with the study procedures or compromise safety. Vitamins and minerals including the use of calcium and/or vitamin D for osteoporosis prevention are allowed.
  Subjects who have been diagnosed with osteoporosis (previously or results from screening DEXA for this study with a T score<−2.5). Subjects with osteopenia (with the T-score between −1 and −2.5) will be allowed to participate in this study.
  Subjects who are not on a stable dose of long- or short-acting bisphosphonates therapy for at least 3 months prior to Screening.
  Subjects who are on raloxifene therapy.
  Subjects who have an abnormality in heart rate, blood pressure, or temperature at Screening and prior to first dose (Treatment Period 1) that in the opinion of the investigator increases the risk of participating in the study. Resting SBP must be 150 mmHg and resting DBP 95 mmHg.
  Subjects who have an abnormality in the 12-lead ECG at Screening and prior to first dose (Treatment Period 1) that in the opinion of the Investigator increases the risk of participating in the study.
  Subjects who have any clinically significant abnormal physical examination finding.
  Subjects who have any clinically significant abnormal laboratory safety findings at Screening or Check-in, upon repeat testing, as determined by the investigator (1 repeat assessment is acceptable).
  Subjects who have ALT or AST>1.5×ULN. For subjects with elevated total bilirubin, direct and indirect bilirubin will be evaluated.
  Subjects with elevated cholesterol or triglyceride levels above the ULN must be determined by the Investigator to be not clinically significant.
  Subjects who have relevant diseases or clinically significant abnormal relevant findings at Screening, as determined by medical history, physical examination, laboratory, ECG, DEXA, and breast and pelvic examination.
  Subjects who have history of any significant chronic disease, such as but not limited to: thrombotic disorders, coronary artery or cerebrovascular disease, liver, kidney or gallbladder dysfunction/disorder(s), diabetes or any other endocrine disease, estrogen dependent neoplasia, post-menopausal uterine bleeding, or endometrial hyperplasia. Subjects with cholecystectomy will be permitted if no medical sequelae post-surgery.
  Subjects who have a history of cancer within the past 5 years with the exception of non-melanoma skin cancer.
  Subjects who have a history of drug-dependence, and recent history of alcoholism or abuse of alcohol.
  Subjects who have a positive result for hepatitis B surface antigen (HBsAg), hepatitis B core antibody, hepatitis C antibody, or human immunodeficiency virus (HIV) antibodies.
  Subjects with a positive drugs of abuse screen or alcohol breath test at Screening (urine will be screened for the presence of the following: amphetamine, barbiturates, benzodiazepines, cannabinoid, cocaine, opiates, phencyclidine, and methadone).
  Subjects with a history of, or difficulty of, access to veins for venipuncture.
  Subjects who have donated blood in the 30 days prior to first dose (Treatment Period 1).
  Subjects who have received blood products within 2 months prior to Screening.
  Subjects who have received a drug in research or have participated in other clinical trials within 30 days, or 5 half-lives (whichever is longer) prior to dosing (Treatment Period 1).

Subjects who have previously taken part in or have withdrawn from this study. (Subjects who have been screened for but not included in a cohort or subjects who dropped out from screening in a previous cohort for non-medical reasons may be eligible to be included in subsequent cohorts.)

Any other unspecified reason that, in the opinion of the investigator (or designee) or Sponsor, makes the subject unsuitable for enrollment.

PK Results

Letrozole plasma concentrations have been analyzed up to Day 897 and Day 729 following a single intramuscular (IM) injection of Letrozole ISM 50 mg and 100 mg, respectively. Moreover, plasma levels of letrozole has also been analyzed for up to 897 and 729 days. The majority of subjects had sustained quantifiable letrozole plasma concentrations up to the last sampling time points reported in both groups (FIG. 8). Dose-normalized peak exposure (Cmax/D) is comparable between both dose strength of Letrozole ISM. Accordingly, the implant or sustained release composition of the invention provides measurable and therapeutic plasma concentrations levels of letrozole for at least about 2 years, at least about 2.5 years, at least about 2.7 years or at least about 2.8 years.

The invention claimed is:

1. A kit for preparing an injectable depot composition, the kit comprising PLA (polylactic acid) particles, solvent for PLA, and drug particles, wherein prior to mixing the PLA particles, solvent for PLA, and drug particles, the drug has a particle size distribution that approximates the PLA's particle size distribution, and after mixing the PLA, solvent for PLA, and drug, the PLA is dissolved in the solvent, wherein the solvent is dimethyl sulfoxide (DMSO), and said drug is selected from the group consisting of letrozole, anastrozole, salt of either thereof, and metabolite of either thereof, and further wherein prior to mixing the PLA particles with said solvent for PLA, the particle size distribution of the PLA particles is defined as follows:
   a) particle size mass distribution with not more than 10% above 300 microns when measured by analytical sieving according to USP<786>;
   b) particle size mass distribution with not more than 10% above 250 microns when measured by analytical sieving according to USP<786>;
   c) particle size volume distribution with a D90 not above 330 microns when measured by laser diffraction analysis;
   d) particle size volume distribution with a D90 not above 280 microns when measured by laser diffraction analysis;
   e) particle size mass distribution where not more than 80% of the particles have a particle size below 125 microns, when measured by analytical sieving according to USP<786>;
   f) a particle size volume distribution with a D80 not below 135 microns when measured by laser diffraction analysis;
   g) particle size mass distribution with not more than 10% above 300 microns, and where not more than 80% of the particles have a particle size below 125 microns, when measured by analytical sieving according to USP<786>; and/or
   h) particle size volume distribution with a D90 not above 330 microns when measured by laser diffraction analysis and with a D80 not below 135 microns when measured by laser diffraction analysis.

2. The kit according to claim 1, wherein the kit comprises at least a first container and a second container, wherein a) the first container contains the drug particles and PLA particles, and the second contains the solvent; or b) the first container contains the drug particles, the second contains PLA particles, and the solvent is in the first container, the second container, and/or in a third container.

3. A method of preparing an injectable depot composition, the method comprising a) providing the kit of claim 1; and b) mixing the components of the containers of the kit, thereby forming said injectable depot composition.

4. The method of claim 3, further comprising sterilizing the DMSO and PLA prior to said mixing.

5. The method of claim 4, wherein said sterilizing is achieved by beta irradiation or filtration.

6. An injectable depot composition consisting essentially of a) 15-35 wt. % drug, 25-35 wt. % PLA, and 30-60 wt. % dimethyl sulfoxide (DMSO); b) 18-28 wt. % drug, 30-35 wt. % PLA, and 37-52 wt. % DMSO; or c) about 23 to about 27 wt. % drug, about 28 to about 34 wt. % PLA, and about 41 to about 47 wt. % DMSO; wherein the weight percentages are with respect to the total weight of said composition; said drug is selected from the group consisting of letrozole, anastrozole, salt of either thereof, and metabolite of either thereof; and prior to mixing with said DMSO the PLA is comprised of particles having a particle size distribution defined as follows:
   a) particle size mass distribution with not more than 10% above 300 microns when measured by analytical sieving according to USP<786>;
   b) particle size mass distribution with not more than 10% above 250 microns when measured by analytical sieving according to USP<786>;
   c) particle size volume distribution with a D90 not above 330 microns when measured by laser diffraction analysis;
   d) particle size volume distribution with a D90 not above 280 microns when measured by laser diffraction analysis;
   e) particle size mass distribution where not more than 80% of the particles have a particle size below 125 microns, when measured by analytical sieving according to USP<786>;
   f) a particle size volume distribution with a D80 not below 135 microns when measured by laser diffraction analysis;
   g) particle size mass distribution with not more than 10% above 300 microns, and where not more than 80% of the particles have a particle size below 125 microns, when measured by analytical sieving according to USP<786>; and/or
   h) particle size volume distribution with a D90 not above 330 microns when measured by laser diffraction analysis and with a D80 not below 135 microns when measured by laser diffraction analysis; and
   wherein after mixing the PLA, solvent for PLA, and drug, the PLA is dissolved in the solvent.

7. The kit of claim 1, wherein said kit forms the injectable depot composition consisting essentially of a) 15-35 wt. % drug, 25-35 wt. % PLA, and 30-60 wt. % DMSO; b) 18-28 wt. % drug, 30-35 wt. % PLA, and 37-52 wt. % DMSO; or c) about 23 to about 27 wt. % drug, about 28 to about 34 wt. % PLA, and about 41 to about 47 wt. % DMSO;
   wherein the weight percentages are with respect to the total weight of said composition.

8. The kit of claim 1, wherein said drug is present in an amount of a) 10 to 500 mg of said drug; b) 10 to 450 mg of said drug; c) 30 to 90 mg of said drug; d) about 50 mg of said drug; e) 80 to 150 mg of said drug; f) about 100 mg of said drug; g) 150 to 250 mg of said drug; h) about 200 mg of said drug; i) 350 to 450 mg of said drug; or j) about 400 mg of said drug.

9. The method of claim 3, wherein the drug is present in said injectable depot composition as a suspension, and the PLA is dissolved in the solvent in said injectable depot composition.

10. The method of claim 3, wherein the PLA has been sized.

11. The composition of claim 6, wherein the PLA is end capped with an ester group.

12. The composition of claim 6, wherein a) the weight ratio of DMSO to PLA is about 1.3:1 to about 1.5:1, or about 1.4:1; b) the weight ratio of DMSO to drug is in the range of about 1.5:1 to about 2:1, about 1.7:1 to about 1.8:1, or about 1.75:1; c) the weight ratio of polymer solution (solvent+PLA) to drug is about 2.8:1 to about 3.2:1, or about 3:1; and/or d) the weight ratio of PLA to drug is about 1.1:1 to about 1.35:1, about 1.1:1 to about 1.3:1, about 1.2:1 to about 1.3:1, or about 1.25:1.

13. The composition of claim 6, wherein said drug is letrozole and implant(s) formed in a subject after administration of said injectable depot composition provides the following pharmacokinetic performance:

| Dose of drug administered (mg) | About 50 | About 100 |
|---|---|---|
| Daily Plasma Concentration from about 2 days after administration (ng/mL) | About 4.5 (about 0.5 to about 13) | About 8.8 (about 1.5 to about 21) |
| Cmax (ng/mL) | About 5 | About 11 |
| Tlag (h) | 0 h | 0 h | wherein Tlag corresponds to the delay between the time of dosing and time of appearance of a measurable concentration of letrozole in the plasma and wherein values are mean values.

14. A kit for preparing an injectable depot composition, the kit comprising PLA (polylactic acid) particles, dimethyl sulfoxide (DMSO), and letrozole particles, wherein prior to mixing the PLA particles, DMSO, and letrozole particles, the letrozole has a particle size distribution that approximates the PLA's particle size distribution, and after mixing the PLA particles, DMSO, and letrozole particles, the PLA is dissolved in the solvent, and wherein
  a) prior to mixing the PLA particles with said solvent for PLA, the PLA particle size distribution is defined as a particle size mass distribution with not more than 10% above 300 microns, and where not more than 80% of the particles have a particle size below 125 microns, when measured by analytical sieving according to USP<786>; and
  b) implant(s) formed in a subject after administration of said injectable depot composition provides the following pharmacokinetic performance:

| Dose of drug administered (mg) | About 50 | About 100 |
|---|---|---|
| Daily Plasma Concentration from about 2 days after administration (ng/mL) | About 4.5 (about 0.5 to about 13) | About 8.8 (about 1.5 to about 21) |
| Cmax (ng/mL) | About 5 | About 11 |
| Tlag (h) | 0 h | 0 h | wherein Tlag corresponds to the delay between the time of dosing and time of appearance of a measurable concentration of letrozole in the plasma and wherein values are mean values.

15. An injectable depot composition consisting essentially of a) 15-35 wt. % letrozole, 25-35 wt. % PLA, and 30-60 wt. % dimethyl sulfoxide (DMSO); b) 18-28 wt. % letrozole, 30-35 wt. % PLA, and 37-52 wt. % DMSO; or c) about 23 to about 27 wt. % letrozole, about 28 to about 34 wt. % PLA, and about 41 to about 47 wt. % DMSO; wherein the weight percentages are with respect to the total weight of said composition; and prior to mixing with said DMSO the PLA is comprised of particles having a particle size distribution defined as follows:
  a) particle size mass distribution with not more than 10% above 300 microns, and where not more than 80% of the particles have a particle size below 125 microns, when measured by analytical sieving according to USP<786>.

* * * * *